(12) United States Patent
Kitamura et al.

(10) Patent No.: US 9,666,808 B2
(45) Date of Patent: May 30, 2017

(54) ORGANIC ELECTROLUMINESCENCE ELEMENT

(71) Applicant: UDC Ireland Limited, Dublin (IE)

(72) Inventors: Yoshitaka Kitamura, Kanagawa (JP); Atsushi Matsunaga, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 520 days.

(21) Appl. No.: 14/240,105

(22) PCT Filed: Sep. 26, 2012

(86) PCT No.: PCT/JP2012/074739
§ 371 (c)(1),
(2) Date: May 13, 2014

(87) PCT Pub. No.: WO2013/047601
PCT Pub. Date: Apr. 4, 2013

(65) Prior Publication Data
US 2014/0299856 A1 Oct. 9, 2014

(30) Foreign Application Priority Data

Sep. 30, 2011 (JP) ................. 2011-218508

(51) Int. Cl.
| | | |
|---|---|---|
| H01L 51/50 | (2006.01) |
| H01L 51/00 | (2006.01) |
| C07D 215/26 | (2006.01) |
| C07C 211/61 | (2006.01) |
| C07D 487/04 | (2006.01) |
| C07D 487/16 | (2006.01) |
| C09K 11/06 | (2006.01) |
| C07D 235/18 | (2006.01) |
| C07D 471/04 | (2006.01) |
| C07D 209/86 | (2006.01) |
| C07D 209/88 | (2006.01) |

(52) U.S. Cl.
CPC ........ *H01L 51/0055* (2013.01); *C07C 211/61* (2013.01); *C07D 209/86* (2013.01); *C07D 209/88* (2013.01); *C07D 215/26* (2013.01); *C07D 235/18* (2013.01); *C07D 471/04* (2013.01); *C07D 487/04* (2013.01); *C07D 487/16* (2013.01); *C09K 11/06* (2013.01); *H01L 51/006* (2013.01); *H01L 51/0058* (2013.01); *H01L 51/0061* (2013.01); *H01L 51/0072* (2013.01); *H01L 51/0094* (2013.01); *C07C 2103/52* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *H01L 51/0051* (2013.01); *H01L 51/0079* (2013.01); *H01L 51/0081* (2013.01); *H01L 51/5016* (2013.01); *H01L 51/5064* (2013.01)

(58) Field of Classification Search
None
See application file for complete search history.

(56) References Cited

U.S. PATENT DOCUMENTS

| | | | | |
|---|---|---|---|---|
| 2005/0221124 A1* | 10/2005 | Hwang | ................. | C07F 9/5728 428/690 |
| 2008/0220285 A1* | 9/2008 | Vestweber | ............. | C07C 13/62 428/690 |
| 2011/0092701 A1 | 4/2011 | Pflumm et al. | | |
| 2012/0097989 A1* | 4/2012 | Lee | .................... | H01L 51/5278 257/88 |

FOREIGN PATENT DOCUMENTS

| | | |
|---|---|---|
| JP | 2005-290000 | 10/2005 |
| JP | 2008-545630 | 12/2008 |
| JP | 2011-523943 | 8/2011 |
| WO | 2011/076314 | 6/2011 |
| WO | 2011/076323 | 6/2011 |

OTHER PUBLICATIONS

International Patent Application No. PCT/JP2012/074739, International Preliminary Report on Patentability, dated Apr. 10, 2014, 11 pages.

* cited by examiner

*Primary Examiner* — Gregory Clark
(74) *Attorney, Agent, or Firm* — Riverside Law LLP

(57) ABSTRACT

An organic electroluminescent element having a small reduction rate in the luminance immediately after the start of light emission is provided. The organic electroluminescent element includes a substrate, a pair of electrodes including an anode and a cathode, disposed on the substrate, a light emitting layer disposed between the electrodes, and at least one organic layer disposed between the light emitting layer and the anode, in which at least one kind of a specific compound including a fluorene structure is contained in at least one organic layer between the light emitting layer and the anode, and at least one kind of a specific compound including a carbazole structure or a fluorene structure is contained as a light emitting material in the light emitting layer.

13 Claims, 1 Drawing Sheet

ORGANIC ELECTROLUMINESCENCE ELEMENT

CROSS-REFERENCE TO RELATED APPLICATIONS

This application is a national stage entry of International Patent Application No. PCT/JP2012/074739, filed 26 Sep. 2012, which in turn claims priority to, and the benefit of, Japanese Patent Application No. 2011-218508, filed 30 Sep. 2011, all of which are incorporated herein by reference in their entireties.

TECHNICAL FIELD

The present invention relates to an organic electroluminescent element.

BACKGROUND ART

Since organic electroluminescent elements (which may hereinafter also be referred to as "elements" or "organic EL elements") are capable of high-luminance light emitting using a low voltage driving, they have been actively researched and developed. The organic electroluminescent elements have organic layers between a pair of electrodes, and utilize, for light emitting, energy of the exciton generated as a result of recombination of electrons injected from a cathode and holes injected from an anode in the organic layer.

In recent years, dope type elements using a light emitting layer in which a light emitting material is doped to a host material have been widely employed.

For example, PTL 1 describes an organic electroluminescent element using a specific compound including a fluorene structure as a light emitting material (dopant) in a light emitting layer.

For example, PTL 2 describes an organic electroluminescent element using a specific compound including a fluorene structure and a carbazole structure as a host material in a light emitting layer.

In addition, PTL 3 also describes a compound including a fluorene structure or a carbazole structure.

CITATION LIST

Patent Literature

[PTL 1] JP-T-2008-545630
[PTL 2] JP-A-2005-290000
[PTL 3] KR-A-2010-0006072

SUMMARY OF INVENTION

Technical Problem

Organic electroluminescent elements in the related art, when subjected to a constant current drive and observed for the reduction of luminance, tend to have a high reduction rate in the luminance immediately after the start of light emission (a short time taken until the luminance is reduced to 90% of the initial value), and then a gradual reduction in the luminance. The reduction in the luminance in this initial stage is referred to as an "initial drop". This initial drop becomes a cause of a so-called "burning", in which a reduction in the luminance in a pixel group exposed to continuous lighting by a fixed image pattern or the like is recognized by an observer as a difference in the luminance level from the peripheral pixels when the organic electroluminescent element is applied to a display. Accordingly, in order to commercialize the organic electroluminescent element in a television set or the like, it is necessary to prevent the burning, and thus it becomes important to suppress the initial drop in the driving durability.

In the related art, as the index of the durability of the organic electroluminescent element, there were many cases where the time (half-time) until the luminance is reduced to 50% of the initial value is investigated, but the initial drop has not been sufficiently investigated.

The present invention is made in consideration of solving the problems and an object thereof is to provide an organic electroluminescent element, which has a small reduction rate in the luminance immediately after the start of light emission.

Solution to Problem

The present inventors have investigated and have thus found that the above-described problems can be solved by incorporating a specific compound including a carbazole structure or a fluorene structure as a light emitting material into a light emitting layer, and incorporating a specific compound including a fluorene structure into a layer on an anode side rather than the light emitting layer. That is, the present invention can be solved by the following means.

[1]

An organic electroluminescent element including a substrate, a pair of electrodes including an anode and a cathode, disposed on the substrate, a light emitting layer disposed between the electrodes, and at least one organic layer disposed between the light emitting layer and the anode, in which at least one kind of compound represented by the following general formula (A) is contained in at least one organic layer disposed between the light emitting layer and the anode, and at least one kind of compound represented by the following general formula (B1-1), (B1-2), or (B1-3) is contained as a light emitting material in the light emitting layer.

[Chem. 1]

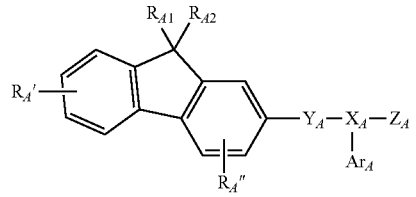

In the general formula (A), $Z_A$ represents a group of any one kind selected from the following general formulae $(Z_A\text{-}1)$, $(Z_A\text{-}2)$, and $(Z_A\text{-}3)$. In the following general formula $(Z_A\text{-}1)$, $(Z_A\text{-}2)$, or $(Z_A\text{-}3)$; * represents a binding site to $X_A$ in the general formula (A).

[Chem. 2]

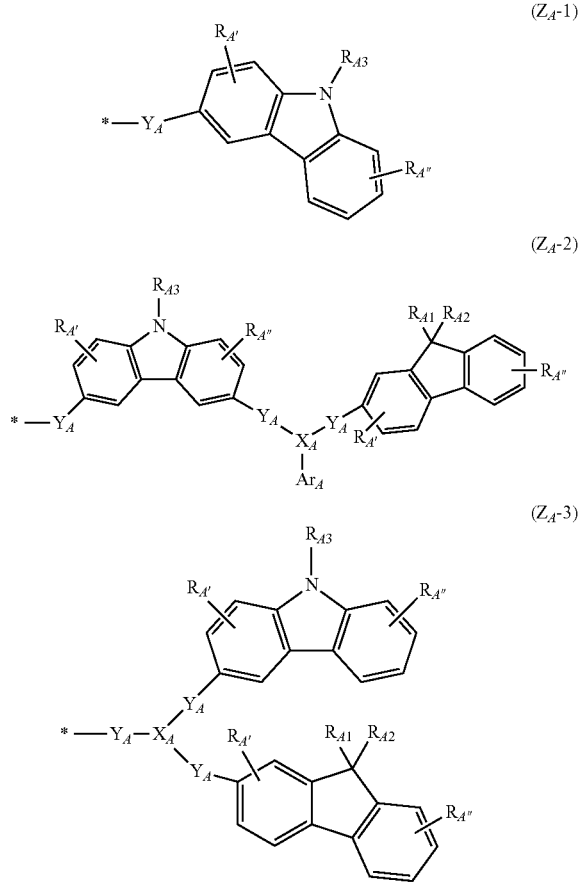

(Z$_A$-1)

(Z$_A$-2)

(Z$_A$-3)

represented by the following general formula (Ar$_A$-1). In the following general formula (Ar$_A$-1), * represents a binding site to X$_A$.

[Chem. 3]

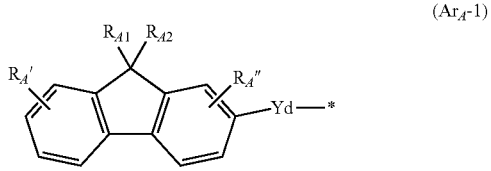

(Ar$_A$-1)

In the general formulae (A), (Z$_A$-1), (Z$_A$-2), (Z$_A$-3), and (Ar$_A$-1), X$_A$'s each independently represent a nitrogen atom, a bromine atom, or a phosphor atom.

Y$_A$ and Yd each independently represent a single bond, a substituted or unsubstituted alkylene group having 1 to 30 carbon atoms, a substituted or unsubstituted arylene group having 6 to 30 carbon atoms, or a substituted or unsubstituted heterocyclic group having 4 to 30 carbon atoms.

R$_{A1}$, R$_{A2}$, and R$_{A3}$ each independently represent a hydrogen atom, a substituted or unsubstituted alkyl group having 1 to 30 carbon atoms, a substituted or unsubstituted aryl group having 6 to 30 carbon atoms, or a substituted or unsubstituted heterocyclic group having 4 to 30 carbon atoms, and the adjacent groups out of R$_{A1}$, R$_{A2}$, and R$_{A3}$ may be bonded to each other to form a saturated or unsaturated carbocycle.

R$_A$' and R$_A$" each independently represent a hydrogen atom, a hydroxyl group, a substituted or unsubstituted alkyl group having 1 to 30 carbon atoms, or a substituted or unsubstituted aryl group having 6 to 30 carbon atoms.

[Chem. 4]

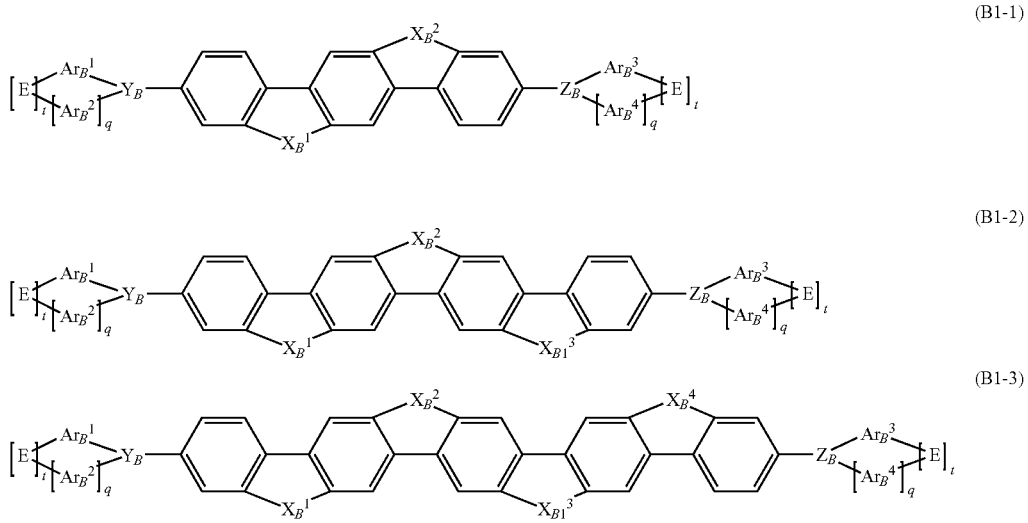

(B1-1)

(B1-2)

(B1-3)

In the general formulae (A) and (Z$_A$-2), Ar$_A$'s are each independently a substituted or unsubstituted aryl group, a substituted or unsubstituted heteroaryl group, or a group In the general formulae (B1-1), (B1-2), and (B1-3), X$_B^1$, X$_B^2$, X$_B^3$, and X$_B^4$ each independently represent B(R$_B^1$), C(R$_B^1$)$_2$, S(R$_B^1$)$_2$, C=O, C=NR$_B^1$, C=C(R$_B^1$)$_2$, O, S, S=O, SO$_2$, N(R$_B^1$), P(R$_B^1$), P(=O)R$_B^1$, P(=S)R$_B^1$, or a group formed by a combination of 2 to 4 groups out of these groups.

Y$_B$ and Z$_B$ each independently represent N, P, P=O, PF$_2$, P=S, As, As=O, As=S, Sb, Sb=O, Sb=S, C=O, O, S, Se, Te, S=O, SO$_2$, SeO$_2$, Te=O, or TeO$_2$.

Ar$_B^1$, Ar$_B^2$, Ar$_B^3$, and Ar$_B^4$ each independently represent an aromatic hydrocarbon ring group or an aromatic heterocyclic group.

E's each independently represent a single bond, N(R$_B^1$), O, S, C(R$_B^1$)$_2$, Si(R$_B^1$)$_2$, or B(R$_B^1$).

R$_B^1$'s each independently represent a hydrogen atom or a substituent.

q and r each independently represent 0 or 1.

t's each independently represent 0 or 1.

[2]

The organic electroluminescent element as described in [1], in which the compound represented by the general formula (B1-1), (B1-2), or (B1-3) is represented by the following general formula (B2-1), (B2-2), or (B2-3).

[Chem. 6]

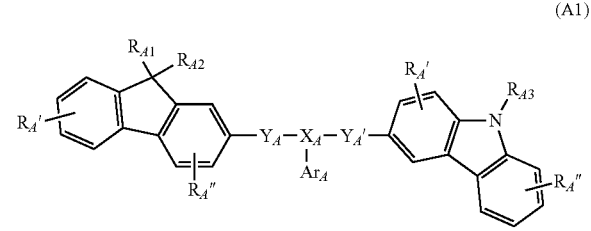

(A1)

In the general formula (A1), Ar$_A$, X$_A$, Y$_A$, R$_{A1}$, R$_{A2}$, R$_{A3}$, R$_A$', and R$_A$" have the same meanings as Ar$_A$, X$_A$, Y$_A$, R$_{A1}$, R$_{A2}$, R$_{A3}$, R$_A$', and R$_A$" in the general formula (A). Y$_A$' has the same meaning as Y$_A$.

[Chem. 5]

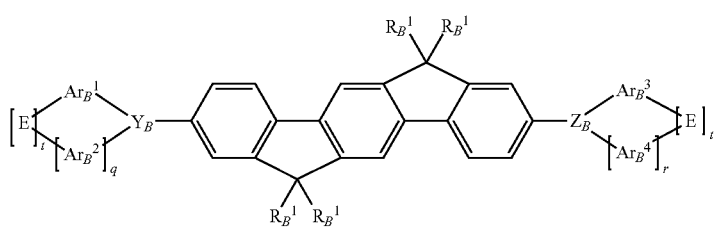

(B2-1)

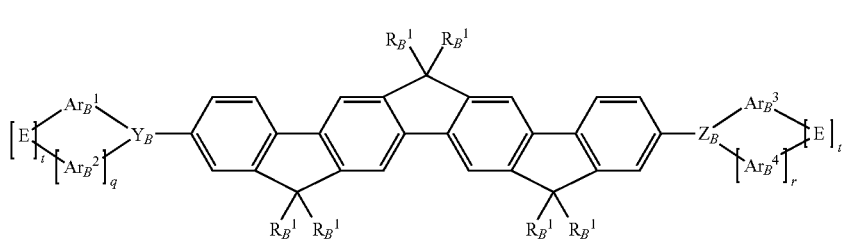

(B2-2)

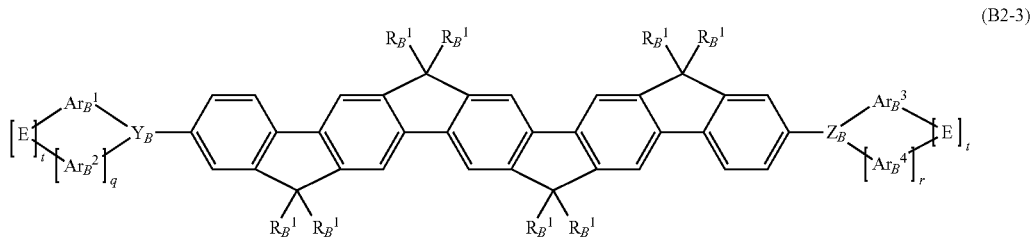

(B2-3)

In the general formulae (B2-1), (B2-2), and (B2-3), Y$_B$, Z$_B$, Ar$_B^1$, Ar$_B^2$, Ar$_B^3$, Ar$_B^4$, E, R$_B^1$, q, r, and t have the same meanings as Y$_B$, Z$_B$, Ar$_B^1$, Ar$_B^2$, Ar$_B^3$, Ar$_B^4$, E, R$_B^1$, q, r, and t in the general formulae (B1-1), (B1-2), and (B1-3).

[3]

The organic electroluminescent element as described in [1] or [2], in which the compound represented by the general formula (A) is represented by the following general formula (A1).

[4]

The organic electroluminescent element as described in any one of [1] to [3], in which X$_A$ in the general formula (A) or (A1) represents a nitrogen atom.

[5]

The organic electroluminescent element as described in any one of [1] to [4], in which Ar$_A$ in the general formula (A) or (A1) represents a substituted or unsubstituted aryl group.

[6]

The organic electroluminescent element as described in any one of [1] to [5], in which $Y_A$, Yd, and $Y_A'$ in the general formula (A) or (A1) each independently represent a single bond or an unsubstituted arylene group having 6 to 12 carbon atoms.

[7]

The organic electroluminescent element as described in any one of [1] to [6], in which $R_{A1}$, and $R_{A2}$ in the general formula ($Z_A$-1), ($Z_A$-2), ($Z_A$-3), or (A1) each independently represent a substituted or unsubstituted alkyl group having 1 to 30 carbon atoms, or a substituted or unsubstituted aryl group having 6 to 30 carbon atoms.

[8]

The organic electroluminescent element as described in any one of [1] to [7], in which $R_{A3}$'s in the general formula ($Z_A$-1), ($Z_A$-2), ($Z_A$-3), or (A1) each independently represent a substituted or unsubstituted aryl group having 6 to 30 carbon atoms.

[9]

The organic electroluminescent element as described in any one of [1] to [8], in which $Y_B$ and $Z_B$ in the general formula (B1-1), (B1-2), (B1-3), (B2-1), (B2-2), or (B2-3) represent N.

[10]

The organic electroluminescent element as described in any one of [1] to [9], in which $Ar_B^1$, $Ar_B^2$, $Ar_B^3$, and $Ar_B^4$ in the general formula (B1-1), (B1-2), (B1-3), (B2-1), (B2-2), or (B2-3) each independently represent an aromatic hydrocarbon ring group.

[11]

A light emitting device using the organic electroluminescent element as described in any one of [1] to [10].

[12]

A display device using the organic electroluminescent element as described in any one of [1] to [10].

[13]

An illumination device using the organic electroluminescent element as described in any one of [1] to [10].

Advantageous Effects of Invention

According to the present invention, an organic electroluminescent element having a small initial drop in the driving durability can be provided.

DESCRIPTION OF EMBODIMENTS

Figure 1:
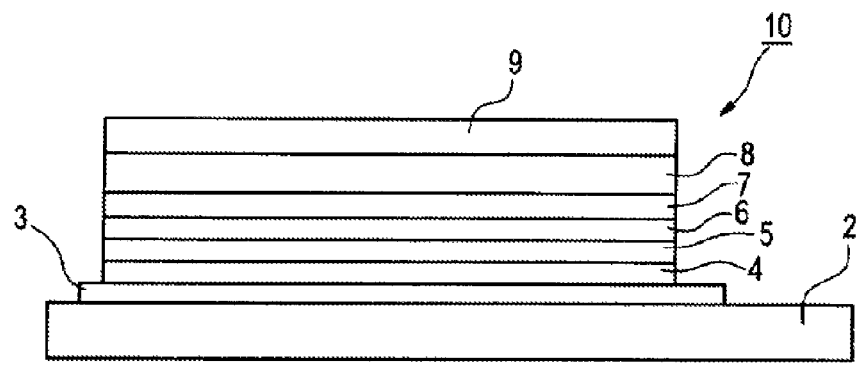
FIG. 1 is a schematic view showing one example of a configuration of an organic electroluminescent element according to the present invention.

In the descriptions of the general formula (A), and the general formulae (B1-1), (B1-2), and (B1-3), the hydrogen atom includes isotopes thereof (deuterium atom and the like), and the atom additionally constituting the substituent includes isotopes thereof.

In the present invention, the Substituent Group A is defined as follows.

(Substituent Group A)

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, cyclohexyl, and neopentyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, 4-methylphenyl, 2,6-dimethylphenyl, naphthyl, and anthranyl), an amino group (preferably having 0 to 30 carbon atoms, more preferably having 0 to 20 carbon atoms, and particularly preferably having 0 to 10 carbon atoms; for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms; for example, methoxy, ethoxy, butoxy, and 2-ethylhexyloxy), and aryloxy group (preferably having 6 to 30 carbon atoms, more preferably having 6 to 20 carbon atoms, and particularly preferably having 6 to 12 carbon atoms; for example, phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms; for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms; for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms; for example, methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms; for example, phenyloxycarbonyl), an acyloxy group (preferably having 2 to 30 carbon atoms, more preferably having 2 to 20 carbon atoms, and particularly preferably having 2 to 10 carbon atoms; for example, acetoxy and benzoyloxy), an acylamino group (preferably having 2 to 30 carbon atoms, more preferably having 2 to 20 carbon atoms, and particularly preferably having 2 to 10 carbon atoms; for example, acetylamino and benzoylamino), an alkoxycarbonylamino group (preferably having 2 to 30 carbon atoms, more preferably having 2 to 20 carbon atoms, and particularly preferably having 2 to 12 carbon atoms; for example, methoxycarbonylamino), an aryloxycarbonylamino group (preferably having 7 to 30 carbon atoms, more preferably having 7 to 20 carbon atoms, and particularly preferably having 7 to 12 carbon atoms; for example, phenyloxycarbonylamino), a sulfonylamino group (preferably having 1 to 30 carbon atoms, more preferably having 1 to 20 carbon atoms, and particularly preferably having 1 to 12 carbon atoms; for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms; for example, sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms; for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms; for example, methylthio and ethylthio), an arylthio group (preferably having 6 to 30 carbon atoms, more preferably having 6 to 20 carbon atoms, and particularly preferably having 6 to 12 carbon atoms; for example, phenylthio), a heterocyclic thio group (preferably having 1 to 30 carbon atoms, more preferably having 1 to 20 carbon atoms, and particularly preferably having 1 to 12 carbon atoms; for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms; for example, mesyl and tosyl), a sulfinyl group (preferably having 1 to 30 carbon atoms, more preferably having 1 to 20 carbon atoms, and particularly preferably having 1 to 12 carbon atoms; for example, methanesulfinyl and benzenesulfinyl), a ureido group (preferably having 1 to 30 carbon atoms, more preferably having 1 to 20 carbon atoms, and particularly preferably having 1 to 12 carbon atoms; for example, ureido, methylureido, and phenylureido), a phosphoramide group (preferably having 1 to 30 carbon atoms, more preferably having 1 to 20 carbon atoms, and particularly preferably having 1 to 12 carbon atoms; for example, diethylphosphoramide and phenylphosphoramide), a hydroxyl group, amercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazino group, an imino group, a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms; for example, trimethylsilyl and triphenylsilyl), a silyloxy group (preferably having 3 to 40 carbon atoms, more preferably having 3 to 30 carbon atoms, and particularly preferably having 3 to 24 carbon atoms; for example, trimethylsilyloxy and triphenylsilyloxy), and a phosphoryl group (for example, a diphenylphosphoryl group and a dimethylphosphoryl group). These substituents may be further substituted, and examples of the additional substituent include the groups selected from the Substituent Group A as described above.

The organic electroluminescent element of the present invention includes a substrate, a pair of electrodes including an anode and a cathode, disposed on the substrate, a light emitting layer disposed between the electrodes, and at least one organic layer disposed between the light emitting layer and the anode, in which at least one kind of compound represented by the following general formula (A) is contained in at least one organic layer disposed between the light emitting layer and the anode, and at least one kind of compound represented by the general formula (B1-1), (B1-2), or (B1-3) is contained as a light emitting material in the light emitting layer.

In the organic electroluminescent element of the present invention, a mechanism by which there is an effect of a small initial drop in the luminance is not clear, but is presumed that fused ring structure portions having a partial structure similar to the general formula (A), including a fluorene structure or carbazole structure having a compound represented by the following general formula (A) in a specific arrangement, contained in at least one organic layer disposed between the light emitting layer and the anode, and a carbazole structure or fluorene structure of a compound represented by the following general formula (B1-1), (B1-2), or (B1-3), contained in the light emitting layer, are interacted at the interface to improve the stability of the molecules, leading to a reduction in the initial decomposition.

[Compound Represented by General Formula (A)]

Hereinbelow, the compound represented by the general formula (A) will be described.

[Chem. 7]

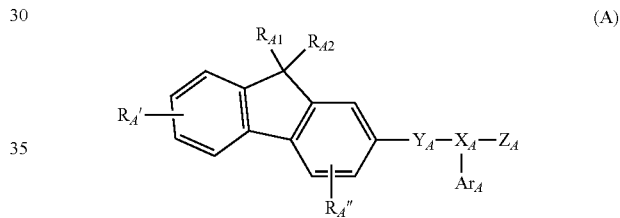

(A)

In the general formula (A), $Z_A$ represents a group of any one kind selected from the following general formulae $(Z_A\text{-}1)$, $(Z_A\text{-}2)$, and $(Z_A\text{-}3)$. In the following general formula $(Z_A\text{-}1)$, $(Z_A\text{-}2)$, or $(Z_A\text{-}3)$, * represents a binding site to $X_A$ in the general formula (A).

[Chem. 8]

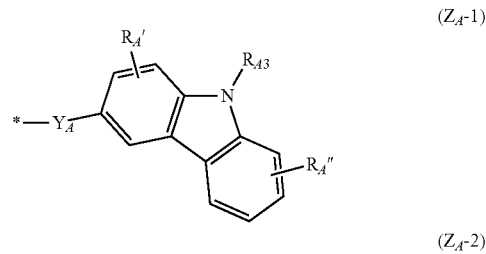

$(Z_A\text{-}1)$

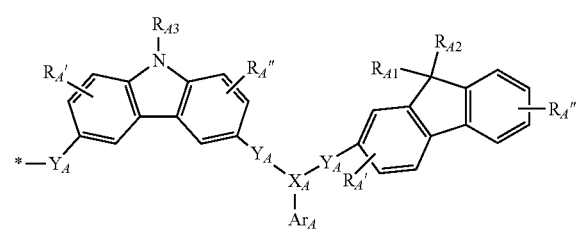

$(Z_A\text{-}2)$

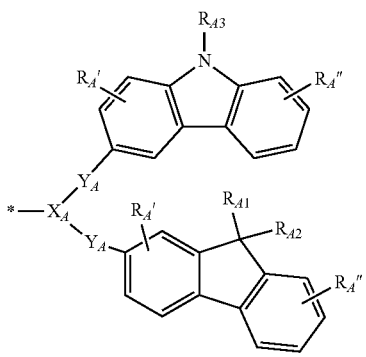

(Z_A-3)

In the general formulae (A) and (Z_A-2), Ar_A's are each independently a substituted or unsubstituted aryl group, a substituted or unsubstituted heteroaryl group, or a group represented by the following general formula (Ar_A-1). In the following general formula (Ar_A-1), * represents a binding site to X_A.

[Chem. 9]

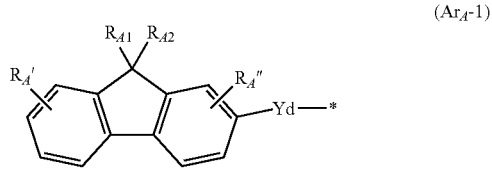

(Ar_A-1)

In the general formulae (A), (Z_A-1), (Z_A-2), (Z_A-3), and (Ar_A-1), X_A's each independently represent a nitrogen atom, a bromine atom, or a phosphor atom. Y_A and Yd each independently represent a single bond, a substituted or unsubstituted alkylene group having 1 to 30 carbon atoms, a substituted or unsubstituted arylene group having 6 to 30 carbon atoms, or a substituted or unsubstituted heterocyclic group having 4 to 30 carbon atoms.

$R_{A1}$, $R_{A2}$, and $R_{A3}$ each independently represent a hydrogen atom, a substituted or unsubstituted alkyl group having 1 to 30 carbon atoms, a substituted or unsubstituted aryl group having 6 to 30 carbon atoms, or a substituted or unsubstituted heterocyclic group having 4 to 30 carbon atoms, and the adjacent groups out of $R_{A1}$, $R_{A2}$, and $R_{A3}$ may be bonded to each other to form a saturated or unsaturated carbocycle.

$R_A'$ and $R_A''$ each independently represent a hydrogen atom, a hydroxyl group, a substituted or unsubstituted alkyl group having 1 to 30 carbon atoms, or a substituted or unsubstituted aryl group having 6 to 30 carbon atoms.

In the general formulae (A) and (Z_A-2), examples of the aryl group or heteroaryl group represented by Ar_A include a phenyl group, a biphenyl group, a pentalenyl group, an indenyl group, a naphthyl group, an anthracenyl group, an azulenyl group, a heptalenyl group, an acenaphthylenyl group, a phenalenyl group, a fluorenyl group, an anthraquinolyl group, an anthryl group, a phenanthryl group, a triphenylene group, apyrenyl group, a chrysenyl group, apicenyl group, aperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovarenyl group, a carbazolyl group, a pyridyl group, a thiophenyl group, a pyrazolyl group, a pyrrolyl group, and an imidazolyl group.

In the general formulae (A) and (Z_A-2), the aryl group or heteroaryl group represented by Ar_A may have a substituent, and examples of the substituent include the groups selected from the Substituent Group A, and particularly preferably an alkyl group having 1 to 3 carbon atoms, an alkoxy group having 1 to 3 carbon atoms, a cyano group, a phenoxy group, a phenyl group, a halogen atom, and an amino group (preferably a diarylamino group, and particularly preferably a diphenylamino group).

Ar_A is preferably a substituted or unsubstituted aryl group, or a group represented by the general formula (Ar_A-1), and more preferably a substituted or unsubstituted aryl group.

Ar_A is preferably a phenyl group, an alkylphenyl group having 1 to 5 carbon atoms, an alkoxyphenyl group having 1 to 5 carbon atoms, a cyanophenyl group, a phenoxyphenyl group, a halophenyl group, a naphthyl group, an alkylnaphthyl group having 1 to 5 carbon atoms, an alkoxynaphthyl group having 1 to 5 carbon atoms, a cyanonaphthyl group, a halonaphthyl group, a phenantolyl group, a fluorenyl group, a carbazolyl group, an alkylcarbazolyl group having 1 to 5 carbon atoms, a biphenyl group, a diphenylaminophenyl group, an alkylbiphenyl group having 1 to 5 carbon atoms, an alkoxybiphenyl group having 1 to 5 carbon atoms, a thiophenyl group, an indolyl group, a pyrazolyl group, or a pyridyl group, more preferably a phenyl group, a biphenyl group, a diphenylaminophenyl group, an alkylphenyl group having 1 to 3 carbon atoms, an alkoxyphenyl group having 1 to 3 carbon atoms, a cyanophenyl group, a phenoxyphenyl group, a halophenyl group, a naphthyl group, an alkylnaphthyl group having 1 to 3 carbon atoms, an alkoxynaphthyl group having 1 to 3 carbon atoms, a cyanonaphthyl group, a halonaphthyl group, a phenanthryl group, a fluorenyl group, or a carbazolyl group, and still more preferably a phenyl group, a biphenyl group, or a diphenylaminophenyl group.

In the general formulae (A), (Z_A-2), and (Z_A-3), X_A's each independently represent a nitrogen atom, a bromine atom, or a phosphorus atom, and preferably a nitrogen atom from the viewpoint of hole transporting properties.

In the general formulae (A), (Z_A-1), (Z_A-2), (Z_A-3), and (Ar_A-1), Y_A and Yd each independently represent a single bond, a substituted or unsubstituted alkylene group having 1 to 30 carbon atoms, a substituted or unsubstituted arylene group having 6 to 30 carbon atoms, or a substituted or unsubstituted heterocyclic group having 4 to 30 carbon atoms.

The alkylene group represented by Y_A and Yd may have a substituent, and in the case where it has a substituent, examples of the substituent include substituents selected from the Substituent Group A, and the substituent is preferably an alkyl group or an aryl group.

The alkylene group having 1 to 30 carbon atoms is preferably an alkylene group having 1 to 10 carbon atoms, and more preferably an alkylene group having 1 to 5 carbon atoms. Examples thereof include a methylene group, an ethylene group, and a propylene group, and among these, a methylene group and an ethylene group are preferred, and a methylene group is more preferred.

The arylene group represented by Y_A and Yd may have a substituent, and in the case where it has a substituent, examples of the substituent include substituents selected from the Substituent Group A, and the substituent is preferably an alkyl group or an aryl group.

The arylene group having 6 to 30 carbon atoms is preferably an arylene group having 6 to 18 carbon atoms, and more preferably an arylene group having 6 to 12 carbon atoms. Examples thereof include a perylene group, a naphthylene group and a biphenylene group, and among these, a phenylene group and a biphenylene group are preferred, and a phenylene group is more preferred.

The heterocyclic group represented by $Y_A$ and Yd may have a substituent, and in the case where it has a substituent, examples of the substituent include substituents selected from the Substituent Group A, and the substituent is preferably an alkyl group or an aryl group.

The heterocyclic group having 4 to 30 carbon atoms is preferably a heterocyclic group having 4 to 15 carbon atoms, and more preferably a heterocyclic group having 4 to 10 carbon atoms. Examples thereof include a pyridinediyl group, a triazolediyl group, a carbazolediyl group, and thiophenediyl group, and among these, a pyridinediyl group and a triazolediyl group are preferred, and a triazolediyl group is more preferred.

$Y_A$ and Yd are preferably a single bond, an unsubstituted arylene group having 6 to 30 carbon atoms, or an unsubstituted heterocyclic group having 4 to 30 carbon atoms, more preferably a single bond or an unsubstituted arylene group having 6 to 12 carbon atoms, and still more preferably a single bond or an unsubstituted phenylene group.

In the general formulae (A), ($Z_A$-1), ($Z_A$-2), ($Z_A$-3), and ($Ar_A$-1), $R_{A1}$, $R_{A2}$, and $R_{A3}$ each independently represent a hydrogen atom, a substituted or unsubstituted alkyl group having 1 to 30 carbon atoms, a substituted or unsubstituted aryl group having 6 to 30 carbon atoms, or a substituted or unsubstituted heterocyclic group having 4 to 30 carbon atoms, and the adjacent groups out of $R_{A1}$, $R_{A2}$, and $R_{A3}$ may be bonded to each other to form a saturated or unsaturated carbocycle.

The alkyl group represented by $R_{A1}$, $R_{A2}$, or $R_{A3}$ may have a substituent, and in the case where it has a substituent, examples of the substituent include substituents selected from the Substituent Group A, and the substituent is preferably an alkyl group or an aryl group.

The alkyl group having 1 to 30 carbon atoms is preferably an alkyl group having 1 to 10 carbon atoms, and more preferably an alkyl group having 1 to 5 carbon atoms. Examples thereof include a methyl group, an ethyl group, a t-butyl group, and an isopropyl group, and among these, a methyl group and a t-butyl group are preferred, and a methyl group is more preferred.

The aryl group represented by $R_{A1}$, $R_{A2}$, and $R_{A3}$ may have a substituent, and in the case where it has a substituent, examples of the substituent include substituents selected from the Substituent Group A, and the substituent is preferably an alkyl group or an aryl group. The aryl group having 6 to 30 carbon atoms is preferably an aryl group having 6 to 18 carbon atoms, and more preferably an aryl group having 6 to 12 carbon atoms. Examples thereof include a phenyl group, a biphenyl group, a naphthyl group, a terphenyl group, an anthryl group, a phenanthryl group, and a fluorenyl group, and among these, a phenyl group, a terphenyl group, a naphthyl group, and a fluorenyl group are preferred, a phenyl group, a terphenyl group, and a fluorenyl group are more preferred, and a phenyl group is still more preferred.

The heterocyclic group represented by $R_{A1}$, $R_{A2}$, and $R_{A3}$ may have a substituent, and in the case where it has a substituent, examples of the substituent include substituents selected from the Substituent Group A, and the substituent is preferably an alkyl group or an aryl group.

The heterocyclic group having 4 to 30 carbon atoms is preferably a heterocyclic group having 4 to 15 carbon atoms, and more preferably a heterocyclic group having 4 to 10 carbon atoms. Examples thereof include a pyridyl group, a carbazolyl group, a triazolyl group, and a benzimidazole group, and among these, a carbazolyl group and a triazolyl group are preferred, and a carbazolyl group is more preferred.

$R_{A1}$, $R_{A2}$, and $R_{A3}$ preferably represent a substituted or unsubstituted alkyl group having 1 to 30 carbon atoms, or a substituted or unsubstituted aryl group having 6 to 30 carbon atoms, and more preferably an unsubstituted alkyl group having 1 to 30 carbon atoms or an unsubstituted aryl group having 6 to 30 carbon atoms.

$R_{A1}$ and $R_{A2}$ more preferably represent an unsubstituted alkyl group having 1 to 30 carbon atoms. Specifically, $R_{A1}$, and $R_{A2}$ particularly preferably represent a methyl group or a phenyl group, and most preferably a methyl group.

$R_{A3}$ more preferably represent an unsubstituted aryl group having 6 to 30 carbon atoms, and most preferably a phenyl group.

In the general formulae (A), ($Z_A$-1), ($Z_A$-2), ($Z_A$-3), and ($Ar_A$-1), $R_A'$ and $R_A''$ each independently represent a hydrogen atom, a hydroxyl group, a substituted or unsubstituted alkyl group having 1 to 30 carbon atoms, or a substituted or unsubstituted aryl group having 6 to 30 carbon atoms.

The alkyl group represented by $R_A'$ and $R_A''$ may have a substituent, and in the case where it has a substituent, examples of the substituent include substituents selected from the Substituent Group A, and the substituent is preferably an alkyl group or an aryl group.

The alkyl group having 1 to 30 carbon atoms is preferably an alkyl group having 1 to 10 carbon atoms, and more preferably an alkyl group having 1 to 5 carbon atoms. Examples thereof include a methyl group, a t-butyl group, and an isopropyl group, and among these, a methyl group and a t-butyl group are preferred, and a methyl group is more preferred.

The aryl group represented by $R_A'$ and $R_A''$ may have a substituent, and in the case where it has a substituent, examples of the substituent include substituents selected from the Substituent Group A, and the substituent is preferably an alkyl group or an aryl group.

The aryl group having 6 to 30 carbon atoms is preferably an aryl group having 6 to 18 carbon atoms, and more preferably an aryl group having 6 to 12 carbon atoms. Examples thereof include a phenyl group, a naphthyl group, and a biphenyl group, and among these, a phenyl group and a biphenyl group are more preferred, and a phenyl group is still more preferred.

$R_A'$ and $R_A''$ are preferably a hydrogen atom, an alkyl group, or an aryl group, and more preferably a hydrogen atom.

From the viewpoint of deposition suitability, in the general formula (A), $Z_A$ is preferably a group represented by the general formula ($Z_A$-1). The compound represented by the general formula (A) is preferably a compound represented by the following general formula (A1).

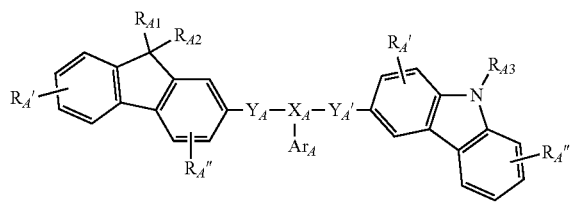

(A1)

In the general formula (A1), $Ar_A$, $X_A$, $Y_A$, $R_{A1}$, $R_{A2}$, $R_{A3}$, $R_A'$ and $R_A''$ have the same meanings as $Ar_A$, $X_A$, $Y_A$, $R_{A1}$, $R_{A2}$, $R_{A3}$, $R_A'$ and $R_A''$ in the general formula (A). $Y_A'$ has the same meaning as $Y_A$.

The specific examples and the preferred examples of $Ar_A$, $X_A$, $Y_A$, $R_{A1}$, $R_{A2}$, $R_{A3}$, $R_A'$ and $R_A''$ in the general formula (A1) are the same as the specific examples and the preferred examples of $Ar_A$, $X_A$, $Y_A$, $R_{A1}$, $R_{A2}$, $R_{A3}$, $R_A'$ and $R_A''$ in the general formula (A).

Hereinbelow, specific examples of the compound represented by the general formula (A) are shown below, but are not limited thereto.

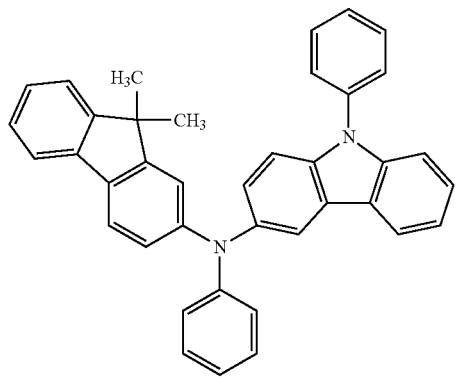

1

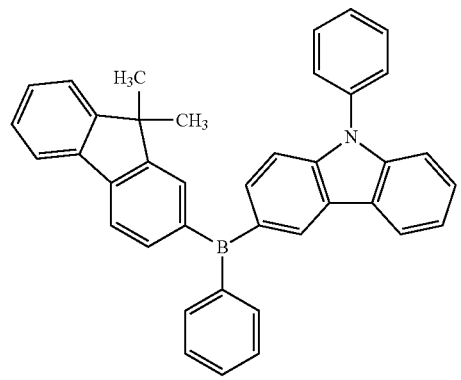

2

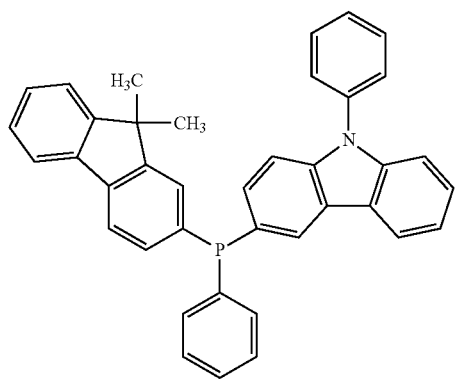

3

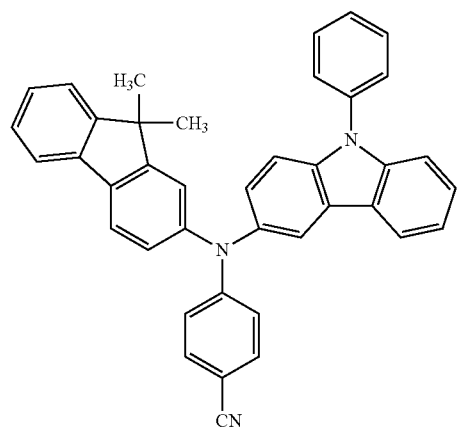

4

-continued
| | |
|---|---|
| 5 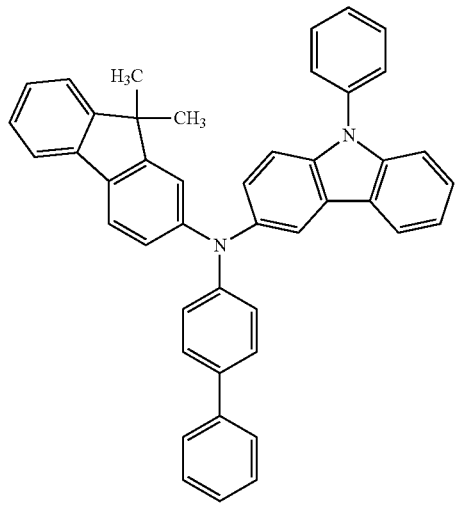 | 6 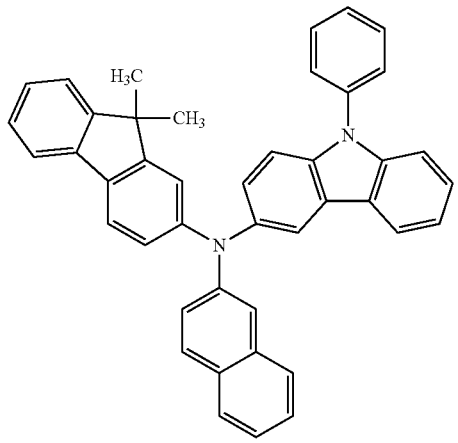 |
| 7 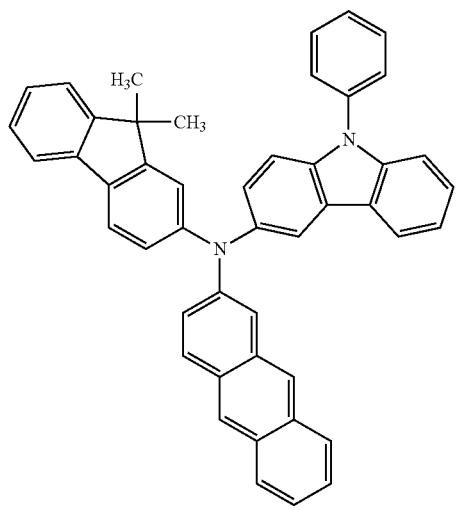 | 8 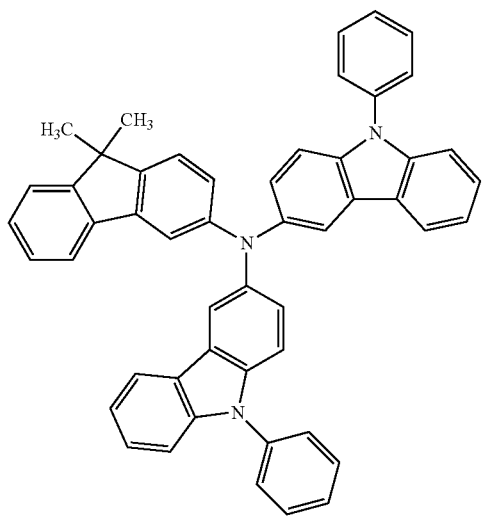 |
| 9 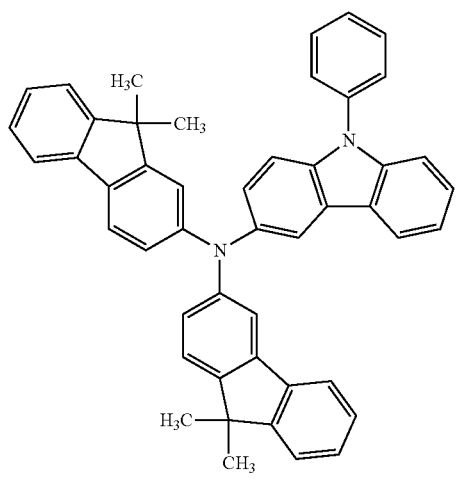 | 10 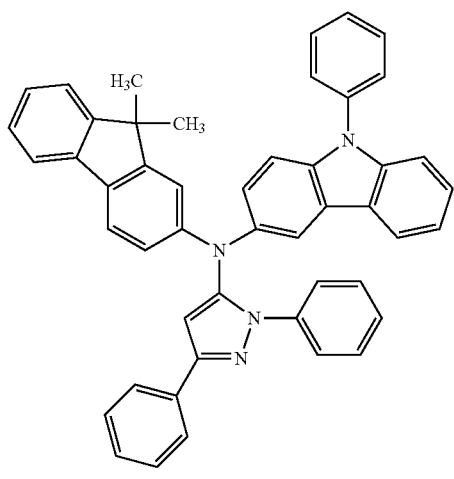 |

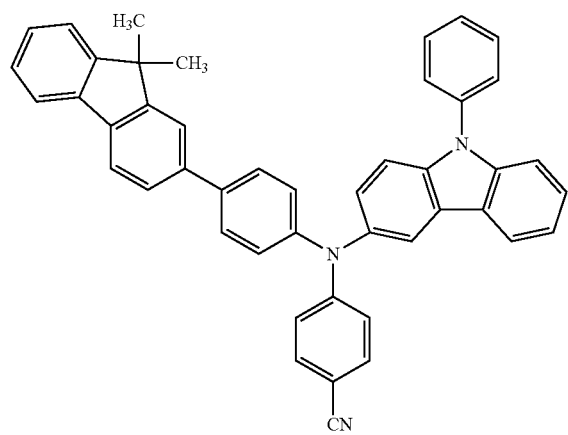
11
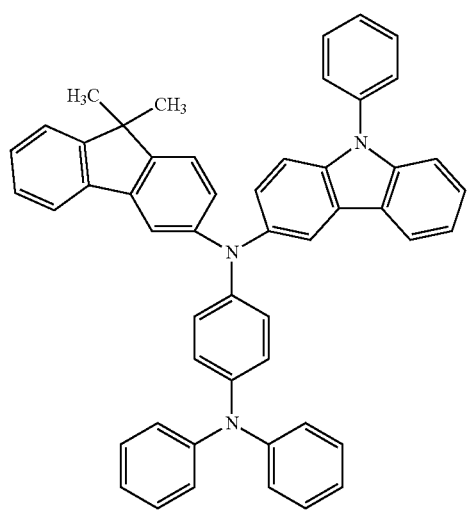
12
[Chem. 12]
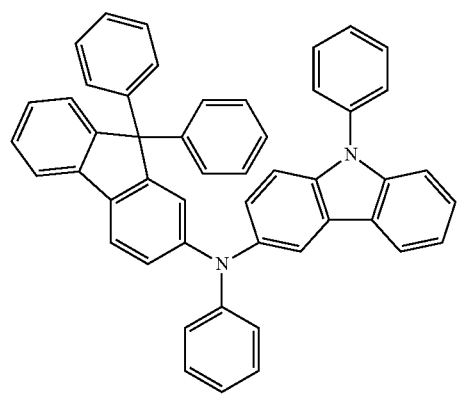
13
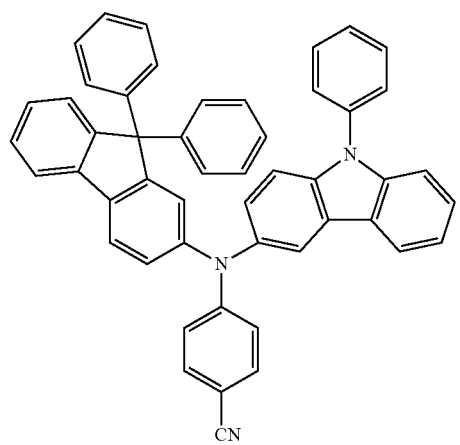
14
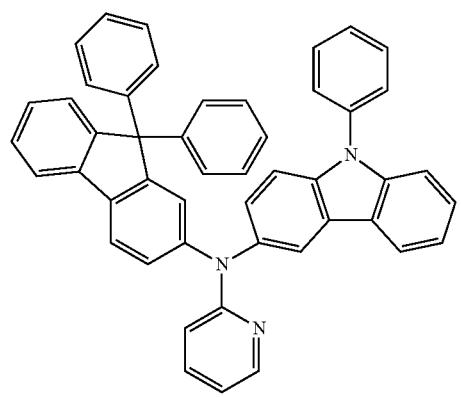
15
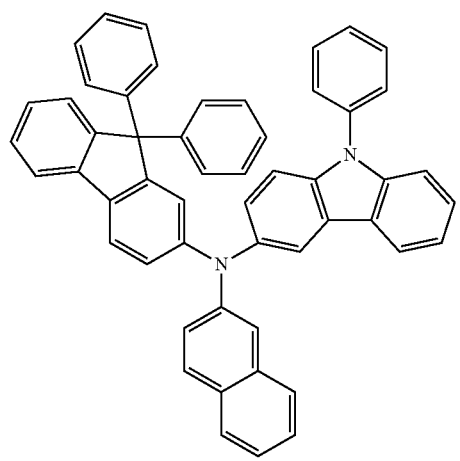
16

-continued
17
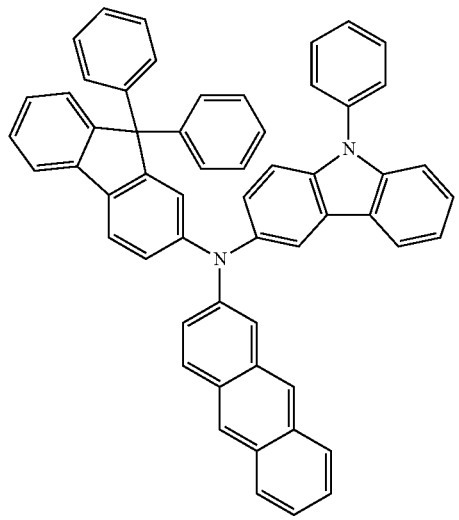
18
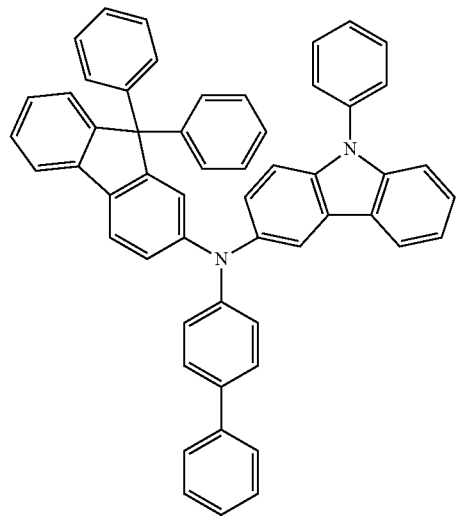
19
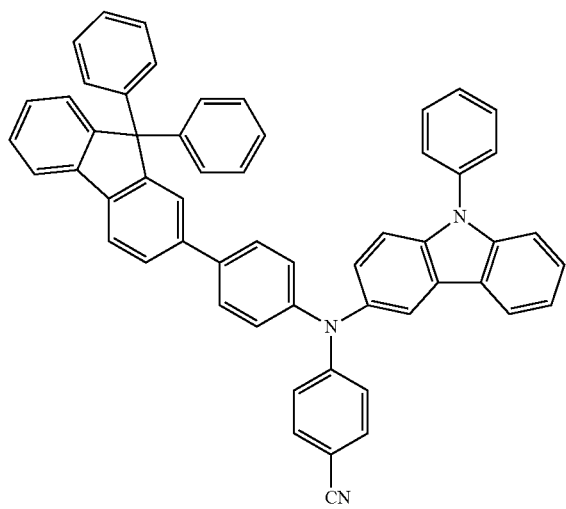
20
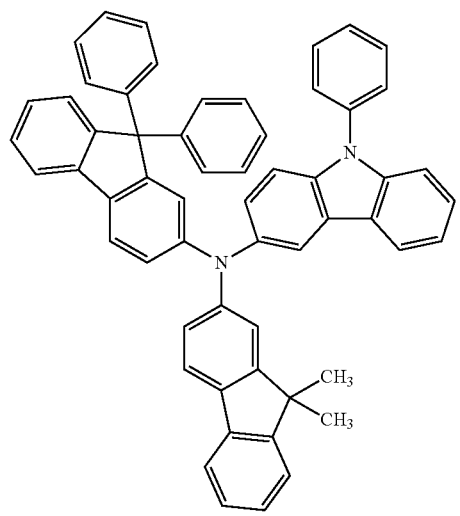
21
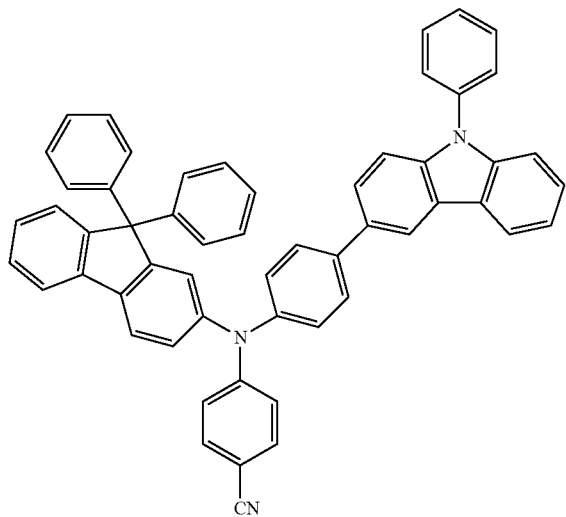
22
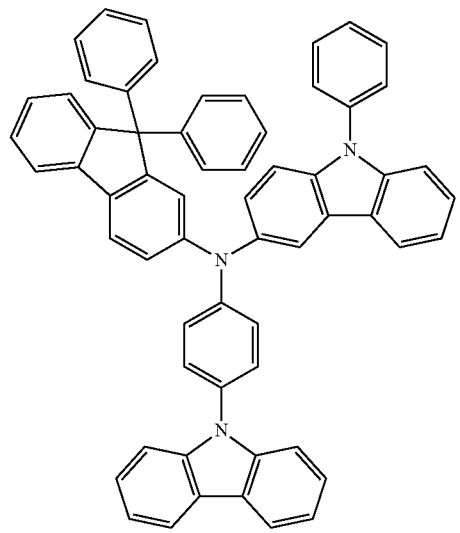

-continued
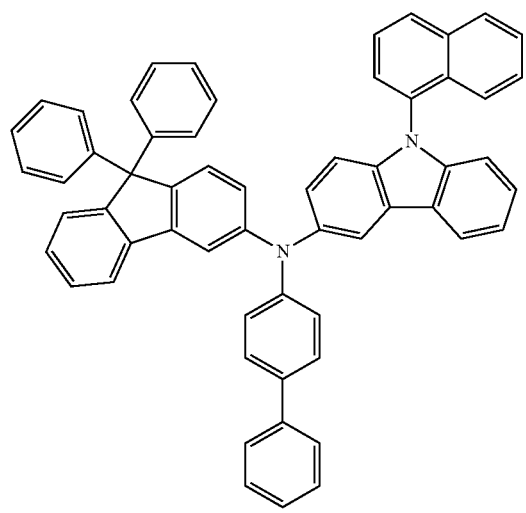
23
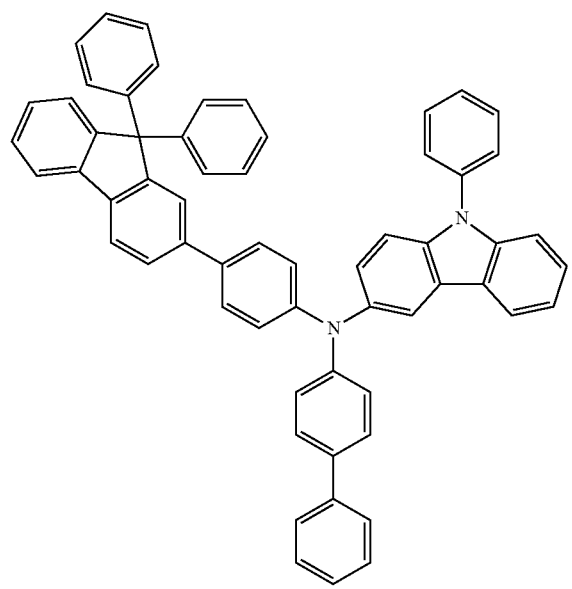
24
[Chem. 13]
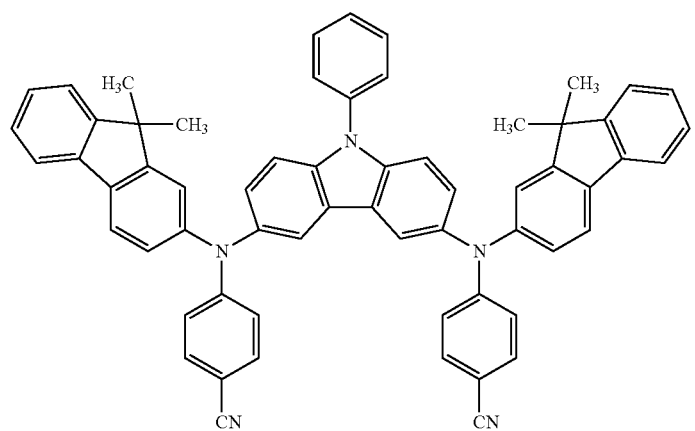
25
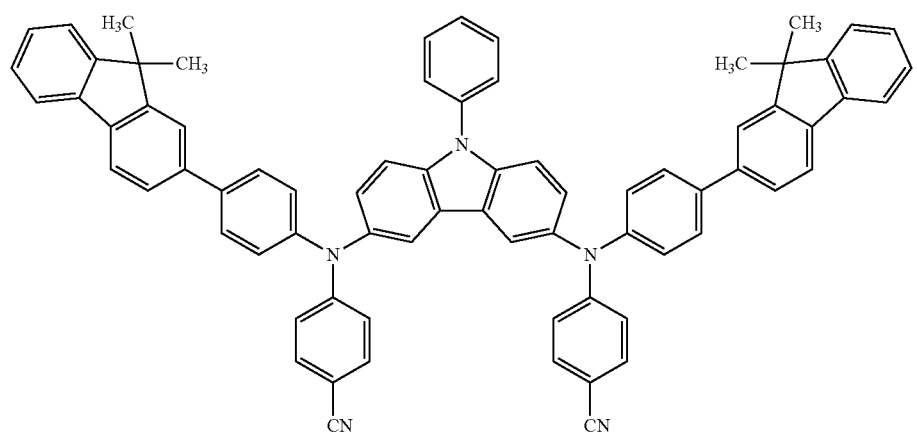
26

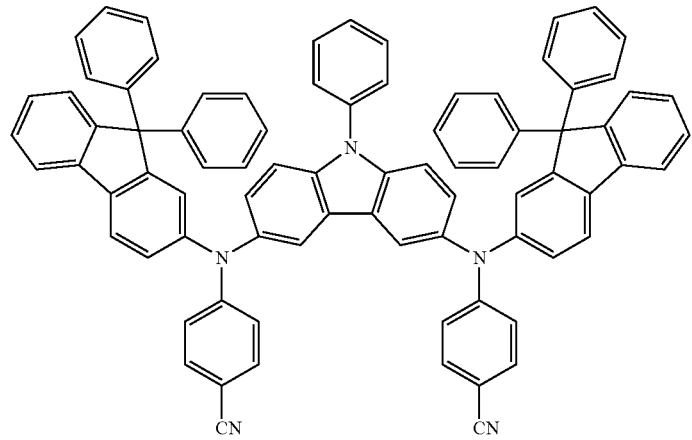
27
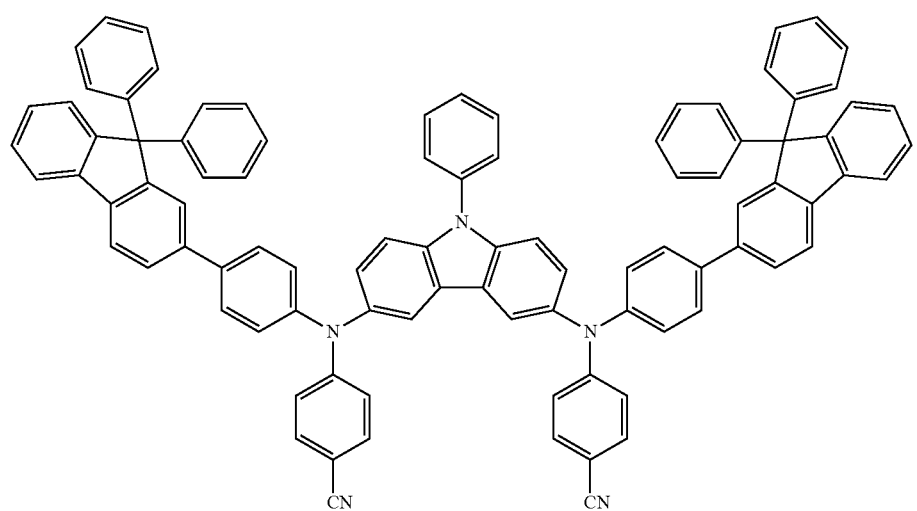
28
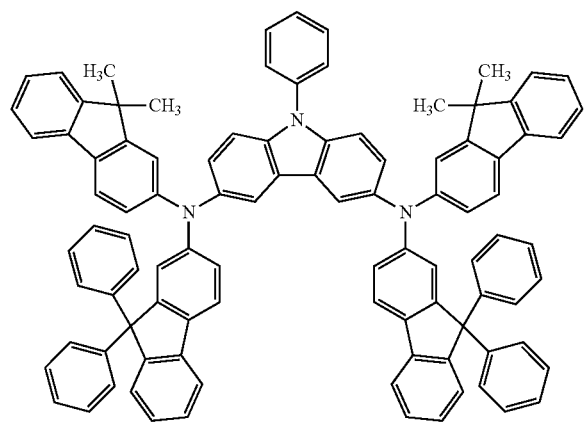
29
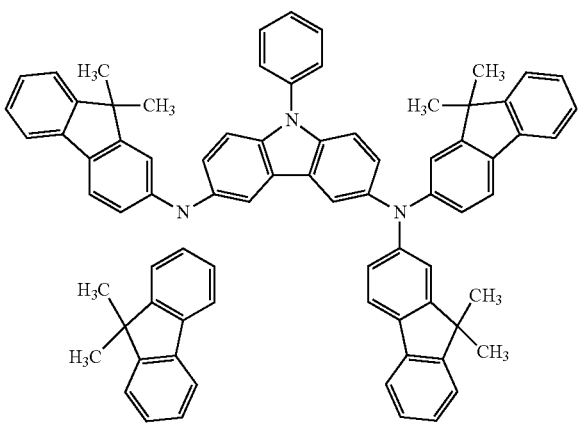
30

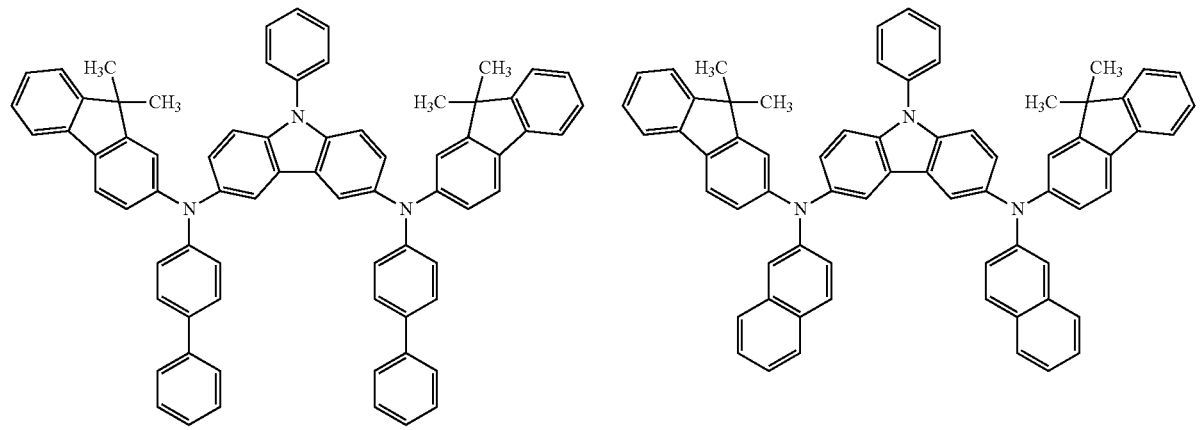
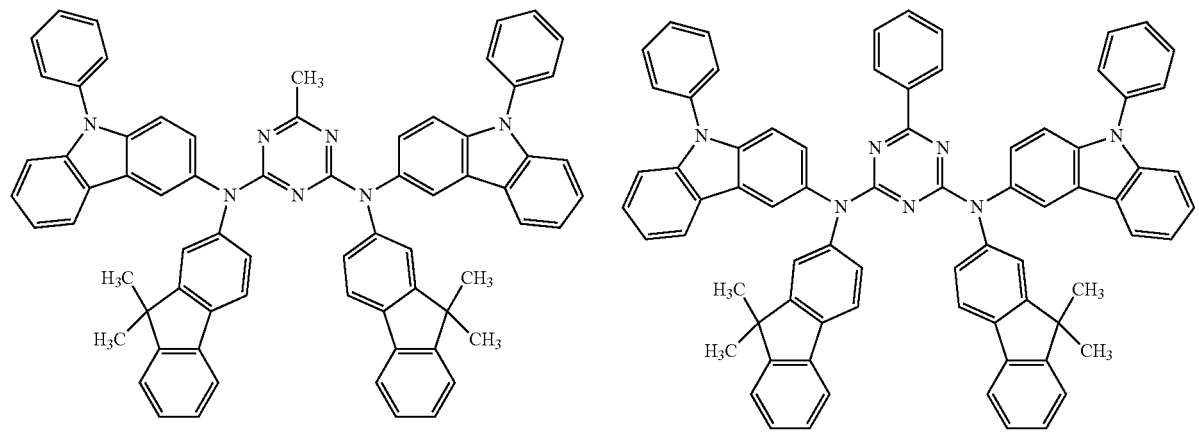
[Chem. 14]
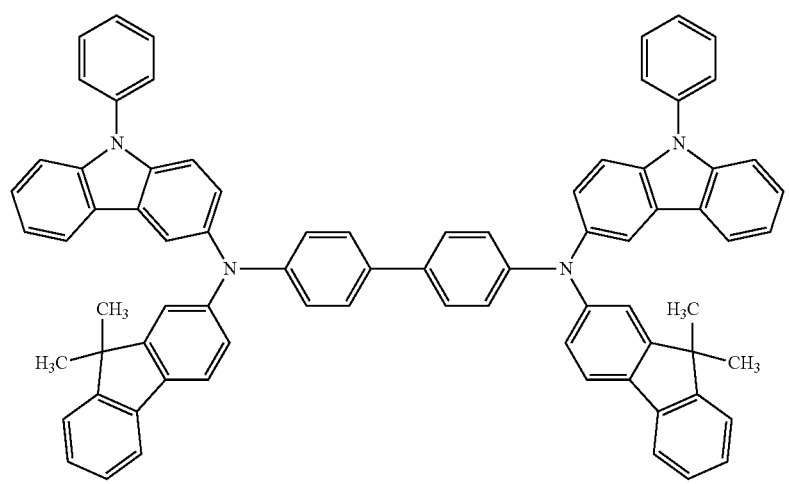

-continued

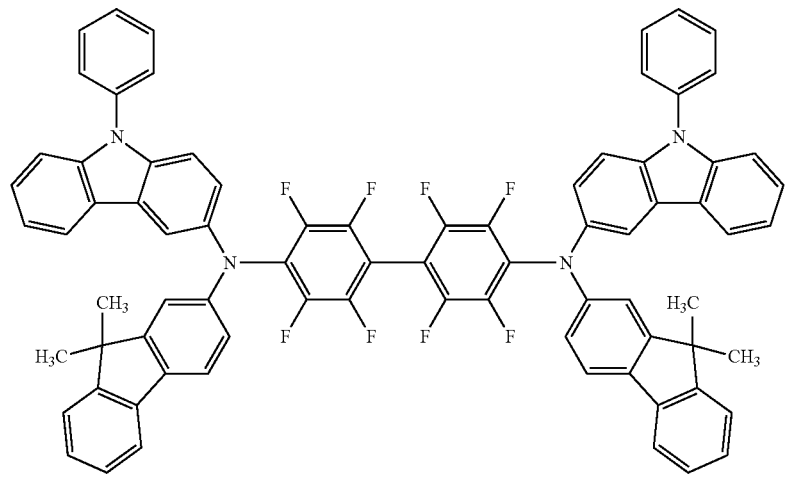

36

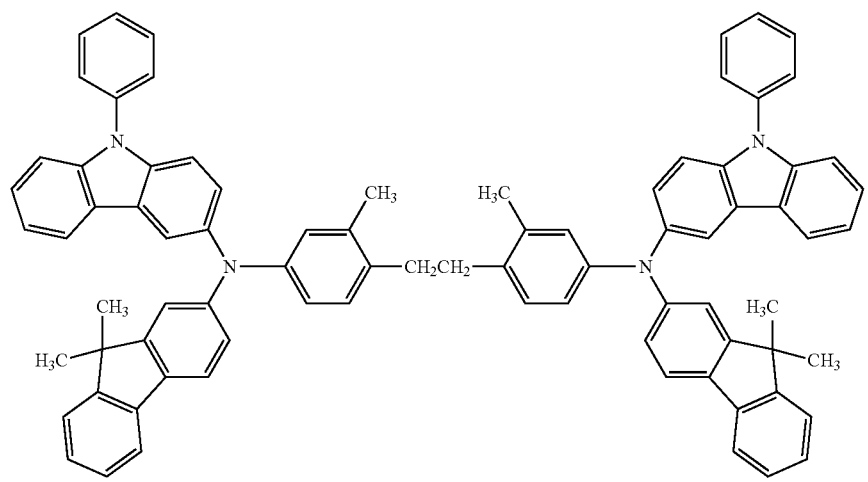

37

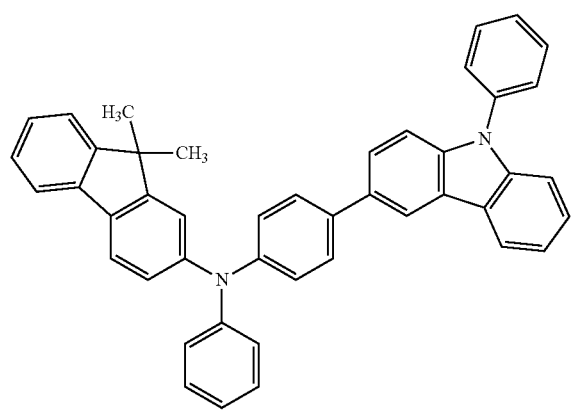

38

39

Examples of the method for preparing a compound represented by the general formula (A) include the methods described in PTL 2.

In the light emitting element of the present invention, the compound represented by the general formula (A) is contained in at least one organic layer disposed between the light emitting layer and the anode, but is not limited in its uses and may be contained in the other layers. The layer to which the compound represented by the general formula (A) according to the present invention is introduced may contain any one or a plurality of a light emitting layer, a hole injecting layer, a hole transporting layer, an electron transporting layer, an electron injecting layer, an exciton blocking layer, and a charge blocking layer.

The compound represented by the general formula (A) is preferably contained in a hole injecting layer or a hole transporting layer, and more preferably in a hole transporting layer. In the case where the compound of the general formula (B1-1), (B1-2), or (B1-3) is contained in the light emitting layer, it is preferable that the compound represented by the general formula (A) be contained in an organic layer on the anode side adjacent to the light emitting layer, from the viewpoint of inhibition of the initial drop.

[Compound Represented by General Formula (B1-1), (B1-2), or (B1-3)]

A compound represented by the following general formula (B1-1), (B1-2), or (B1-3) will be described.

The organic electroluminescent element of the present invention contains a compound represented by the following general formula (B1-1), (B1-2), or (B1-3) as a light emitting material in the light emitting layer.

[Chem. 15]

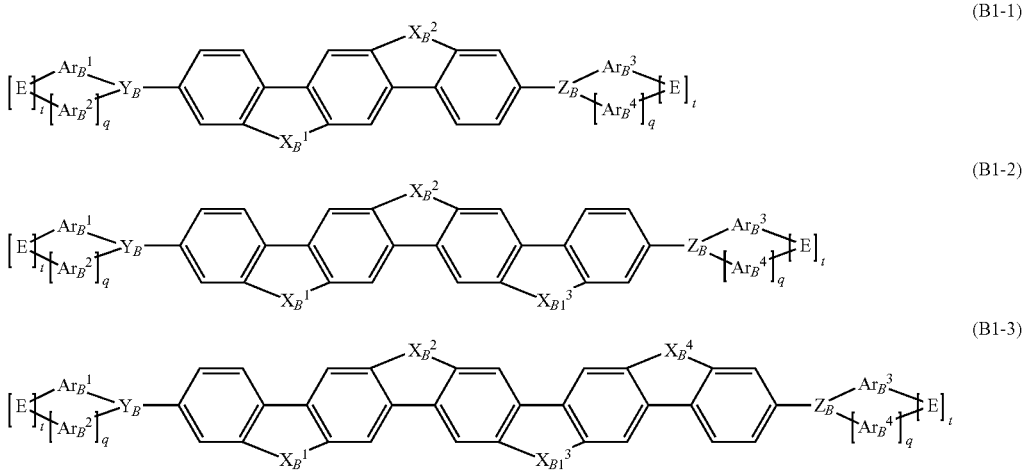

In the general formulae (B1-1), (B1-2), and (B1-3), $X_B^1$, $X_B^2$, $X_B^3$, and $X_B^4$ each independently represent $B(R_B^1)$, $C(R_B^1)_2$, $S(R_B^1)_2$, C=O, C=$NR_B^1$, C=$C(R_B^1)_2$, O, S, S=O, $SO_2$, $N(R_B^1)$, $P(R_B^1)$, P(=O)$R_B^1$, P(=S)$R_B^1$, or a group formed by a combination of 2 to 4 groups out of these groups.

$Y_B$ and $Z_B$ each independently represent N, P, P=O, $PF_2$, P=S, As, As=O, As=S, Sb, Sb=O, Sb=S, C=O, O, S, Se, Te, S=O, $SO_2$, $SeO_2$, Te=O, or $TeO_2$.

$Ar_B^1$, $Ar_B^2$, $Ar_B^3$, and $Ar_B^4$ each independently represent an aromatic hydrocarbon ring group or an aromatic heterocyclic group.

E's each independently represent a single bond, $N(R_B^1)$, O, S, $C(R_B^1)_2$, $Si(R_B^1)_2$, or $B(R_B^1)$.

$R_B^1$'s each independently represent a hydrogen atom or a substituent.

q and r each independently represent 0 or 1.

t's each independently represent 0 or 1.

In the general formulae (B1-1), (B1-2), and (B1-3), $X_B^1$, $X_B^2$, $X_B^3$, and $X_B^4$ each independently represent a group formed by combination of 2 to 4 groups out of $B(R_B^1)$, $C(R_B^1)_2$, $S(R_B^1)_2$, C=O, C=$NR_B^1$, C=$C(R_B^1)_2$, O, S, S=O, $SO_2$, $N(R_B^1)$, $P(R_B^1)$, P(=O)$R_B^1$, and P(=S)$R_B^1$. Here, $R_B^1$'s each independently represent a hydrogen atom or a substituent. $R_B^1$ will be described later.

$X_B^1$, $X_B^2$, $X_B^3$, and $X_B^4$ are preferably each independently $C(R_B^1)_2$, $N(R_B^1)$, $P(R_B^1)$, or P(=O)$R_B^1$, and more preferably $C(R_B^1)_2$ or $N(R_B^1)$, and from the viewpoint of durability until the luminance drops to 90% of the initial luminance, $C(R_B^1)_2$ is still more preferred.

In the general formulae (B1-1), (B1-2), and (B1-3), $Y_B$ and $Z_B$ each independently represent N, P, P=O, $PF_2$, P=S, As, As=O, As=S, Sb, Sb=O, Sb=S, C=O, O, S, Se, Te, S=O, $SO_2$, Se=O, $SeO_2$, Te=O, or $TeO_2$.

$Y_B$ and $Z_B$ are preferably each independently N, C=O, P, or P=O, and more preferably N, C=O, or P=O, and from the viewpoint of charge transporting properties, $Y_B$ and $Z_B$ still more preferably represent N.

In the general formulae (B1-1), (B1-2), and (B1-3), $Ar_B^1$, $Ar_B^2$, $Ar_B^3$, and $Ar_B^4$ each independently represent an aromatic hydrocarbon ring group or an aromatic heterocyclic group, and preferably an aromatic hydrocarbon ring group.

The aromatic hydrocarbon ring group or aromatic heterocyclic group is preferably a group having an aromatic or heterocyclic aromatic ring structure containing 5 to 40 aromatic ring atoms.

The aromatic hydrocarbon ring group is preferably an aromatic hydrocarbon ring group having 5 to 16 carbon atoms, and more preferably an aromatic hydrocarbon ring group having 6 to 12 carbon atoms. Specific examples of the monovalent aromatic hydrocarbon ring group include a phenyl group, a naphthyl group, an anthryl group, a phenanthryl group, and a fluorenyl group, preferably a phenyl group, a naphthyl group, or a fluorenyl group, more preferably a phenyl group, a 1-naphthyl group, or a 2-naphthyl group, and still more preferably a phenyl group. The specific examples and the preferred range of the divalent aromatic hydrocarbon ring group include groups formed by removing any one hydrogen atom from the monovalent aromatic hydrocarbon ring group.

The aromatic heterocyclic group is preferably an aromatic heterocyclic group having 5 to 16 aromatic ring atoms, and more preferably an aromatic heterocyclic group having 4 to 10 aromatic ring atoms. Examples thereof include a pyridyl group, a quinolyl group, a quinoxalyl group, and a carbazolyl group, and among these, a quinolyl group and a quinoxalyl group are preferred, and a quinolyl group is more preferred.

Here, the aromatic hydrocarbon ring group or aromatic heterocyclic group is not a group which necessarily contains only an aromatic hydrocarbon ring or aromatic hetero ring, and further includes a group in which a plurality of aromatic hydrocarbon rings or aromatic hetero rings may be interrupted by, for example, a short non-aromatic unit such as C, N, and O atoms. Accordingly, for example, groups including structures such as 9,9'-spirobifluorene, 9,9-diarylfluorene, triarylamine, and diaryl ether are also considered as aromatic hydrocarbon ring groups or aromatic heterocyclic groups in the present specification.

$Ar_B^1$, $Ar_B^2$, $Ar_B^3$, and $Ar_B^4$ are preferably each independently an aromatic hydrocarbon ring group or aromatic heterocyclic group having 5 to 16 aromatic ring atoms, and more preferably an aromatic hydrocarbon ring group having 5 to 16 aromatic ring atoms. Specifically, they are more preferably groups formed by the removal of any one or two hydrogen atoms from benzene, naphthalene, anthracene, phenanthrene, pyridine, pyrene, thiophene, triphenylamine, diphenyl-1-naphthyl amine, diphenyl-2-naphthylamine, phenyldi(1-naphthyl)amine, phenyldi(2-naphthyl)amine, and spirobifluorene, and still more preferably groups formed by the removal of any one or two hydrogen atoms from benzene or naphthalene (examples of the monovalent groups include a phenyl group, a 1-naphthyl group, and a 2-naphthyl group).

The aromatic hydrocarbon ring group or aromatic heterocyclic group represented by $Ar_B^1$, $Ar_B^2$, $Ar_B^3$, and $Ar_B^4$ may have a substituent, and examples of the substituent include the substituents represented by $R_B^1$ as described later.

In the general formulae (B1-1), (B1-2), and (B1-3), $R_B^1$'s each independently represent a hydrogen atom or a substituent, and preferably H, F, Cl, Br, I, CN, $NO_2$, $N(R_B^2)_2$, $Si(R_B^2)_3$, $B(OR_B^2)_2$, a linear alkyl group having 1 to 40 carbon atoms, an alkoxy group or thioalkoxy group, a branched or cyclic alkyl group having 3 to 40 carbon atoms, an alkoxy group, or a thioalkoxy group (each chain may be substituted with one or more $R_B2$ groups, and one or more non-adjacent $CH_2$ groups may be substituted with $-R_B^2C=CR_B^2-$, $-C\equiv C-$, $Si(R_B^2)_2$, $Ge(R_B^2)_2$, $Sn(R_B^2)_2$, $C=O$, $C=S$, $C=Se$, $C=NR_B^2$, $-O-$, $-S-$, $-CO-O-$, or $CONR_B^2$, and one or more H atoms may be substituted with F, Cl, Br, I, CN or $NO_2$), an aryl group or a heteroaryl group having 5 to 40 aromatic ring atoms, which may be substituted with one or more non-aromatic $R_B^1$ groups, an aryloxy group or heteroaryloxy group having 5 to 40 aromatic ring atoms, which may be substituted with one or more non-aromatic $R_B^1$ groups, or combinations of these structures.

Here, 2 or more substituent $R_B^1$'s may be combined with each other to form a monocyclic or polycyclic ring structure.

The linear alkyl group represented by $R_B^1$ is preferably a linear alkyl group having 1 to 10 carbon atoms, and more preferably a linear alkyl group having 1 to 5 carbon atoms.

The branched or cyclic alkyl group represented by $R_B^1$ is preferably a branched or cyclic alkyl group having 1 to 5 carbon atoms, and more preferably a branched alkyl group having 3 to 5 carbon atoms.

Examples of the alkyl group include a methyl group, an ethyl group, an n-propyl group, i-propyl group, an n-butyl group, an i-butyl group, an s-butyl group, a t-butyl group, a 2-methylbutyl group, an n-pentyl group, an s-pentyl group, a cyclopentyl group, an n-hexyl group, a cyclohexyl group, an n-heptyl group, a cycloheptyl group, an n-octyl group, a cyclooctyl group, a 2-ethylhexyl group, an ethenyl group, a propenyl group, a butenyl group, a pentenyl group, a cyclopentenyl group, a hexenyl group, a cyclohexenyl group, a heptenyl group, a cycloheptenyl group, an octenyl group, a cyclooctenyl group, an ethynyl group, a propynyl group, a butynyl group, apentynyl group, a hexynyl group, and an octynyl group, and among these, a methyl group, a t-butyl group, and an i-propyl group are preferred, and a methyl group and a t-butyl group are more preferred.

The linear alkoxy group represented by $R_B^1$ is preferably a linear alkoxy group having 1 to 5 carbon atoms, and more preferably a linear alkoxy group having 1 to 3 carbon atoms.

The branched or cyclic alkoxy group represented by $R_B^1$ is preferably a branched or cyclic alkoxy group having 3 to 10 carbon atoms, and more preferably a branched or cyclic alkoxy group having 3 to 6 carbon atoms.

Examples of the alkoxy group include a methoxy group, an ethoxy group, an n-propoxy group, an i-propoxy group, an n-butoxy group, an i-butoxy group, an s-butoxy group, a t-butoxy group, and a 2-methylbutoxy group, and among these, a methoxy group and a t-butoxy group are preferred, and a methoxy group is more preferred.

The linear thioalkoxy group represented by $R_B^1$ is preferably a linear thioalkoxy group having 1 to 5 carbon atoms, and more preferably a linear thioalkoxy group having 1 to 3 carbon atoms.

The branched or cyclic thioalkoxy group represented by $R_B^1$ is preferably a branched or cyclic thioalkoxy group having 3 to 10 carbon atoms, and more preferably a branched or cyclic thioalkoxy group having 3 to 6 carbon atoms.

Examples of the thioalkoxy group include a methylthio group, an ethylthio group, and a t-butylthio group, and among these, a methylthio group and a t-butylthio group are preferred, and a methylthio group is more preferred.

Each chain of the alkyl group, alkoxy group, and thioalkoxy group represented by $R_B^1$ may be substituted with one or more $R_B^2$ groups, one or more non-adjacent $CH_2$ groups may be substituted with $-R_B^2C=CR_B^2-$, $-C\equiv C-$, $Si(R_B^2)_2$, $Ge(R_B^2)_2$, $Sn(R_B^2)_2$, $C=O$, $C=S$, $C=Se$, $C=NR_B^2$, $-O-$, $-S-$, $-CO-O-$, or $CONR_B^2$, and further, one or more H atoms may be substituted with F, Cl, Br, I, CN, or $NO_2$.

In the case where one or more non-adjacent $CH_2$ groups are substituted in each chain, they are preferably substituted with $-R_B^2C=CR_B^2-$, $-C\equiv C-$, $-O-$, or $-S-$.

In the case where the H atoms are substituted in each chain, they are preferably substituted with F.

The aryl group represented by $R_B^1$ is preferably an aryl group having 6 to 18 aromatic ring atoms, and more preferably an aryl group having 6 to 12 aromatic ring atoms. Examples thereof include a phenyl group, a naphthyl group, a fluorenyl group, and a biphenyl group, and among these, a phenyl group, a naphthyl group, and a fluorenyl group are preferred, and a phenyl group and a naphthyl group are more preferred.

The aromatic heterocyclic group represented by $R_B^1$ is preferably a heteroaryl group having 4 to 16 aromatic ring atoms, and more preferably a heteroaryl group having 4 to 10 aromatic ring atoms. Examples thereof include a pyridyl group, a quinolyl group, a carbazolyl group, and a quinoxalyl group, and among these, a pyridyl group and a carbazolyl group are preferred, and a pyridyl group is more preferred.

$R_B^1$'s are preferably each independently H, F, CN, a linear alkyl group having 1 to 5 carbon atoms, or a branched alkyl group having 3 to 5 carbon atoms, and in each case, one or more non-adjacent CH$_2$ groups may be substituted with —R$_B^2$C=CR$_B^2$—, —C≡C—, —O—, or —S—, and one or more H atoms may be substituted with F. Further, an aryl group or a heteroaryl group having 5 to 16 aromatic ring atoms, which may be substituted with one or more non-aromatic R$_B^1$ groups, is preferred, and 2 or more R$_B^1$ groups may be combined with each other to form a ring structure.

R$_B^1$ is more preferably H, F, CN, a methyl group, a tert-butyl group, or an aryl group or a heteroaryl group having 4 to 6 carbon atoms, which may be substituted.

R$_B^2$'s each independently represent a hydrogen atom, or an aliphatic hydrocarbon group or aromatic hydrocarbon group having 1 to 20 carbon atoms.

The aliphatic hydrocarbon group having 1 to 20 carbon atoms, represented by R$_B^2$, is preferably an aliphatic hydrocarbon group having 1 to 10 carbon atoms, and more preferably an aliphatic hydrocarbon group having 1 to 5 carbon atoms. Examples thereof include a methyl group, an ethyl group, and a t-butyl group, and among these, a methyl group and a t-butyl group are preferred, and a methyl group is more preferred.

The aromatic hydrocarbon group having 1 to 20 carbon atoms, represented by R$_B^2$, is preferably an aromatic hydrocarbon group having 6 to 18 carbon atoms, and more preferably an aromatic hydrocarbon group having 6 to 12 carbon atoms. Examples thereof include a phenyl group, a naphthyl group, and a biphenyl group, and among these, a phenyl group and a naphthyl group are preferred, and a phenyl group is more preferred.

R$_B^2$ is preferably a methyl group or a phenyl group, and more preferably a methyl group.

In the general formulae (B1-1), (B1-2), and (B1-3), q and r each independently represent 0 or 1. If the corresponding central element of the Y$_B$ or Z$_B$ group is an element in Group 15 in the Periodic Table, q and r are each independently 1, and further, the corresponding central element of the Y$_B$ or Z$_B$ group is an element in Group 14 or 16 in the Periodic Table, q and r each independently represent 0.

As described above, from the viewpoint that Y$_B$ and Z$_B$ represent N, q and r are preferably 1.

In the general formulae (B1-1), (B1-2), and (B1-3), t's each independently represent 0 or 1. Here, if q is 0, t is 0.

In the general formulae (B1-1), (B1-2), and (B1-3), from the viewpoint of deposition suitability, the general formulae (B1-1) and (B1-2) are preferred, and the general formula (B1-1) is more preferred.

The compound represented by the general formula (B1-1), (B1-2), or (B1-3) is preferably a compound represented by the following general formula (B2-1), (B2-2), or (B2-3) from the viewpoint of durability until the initial luminance of the organic EL element is reduced to 90%.

[Chem. 16]

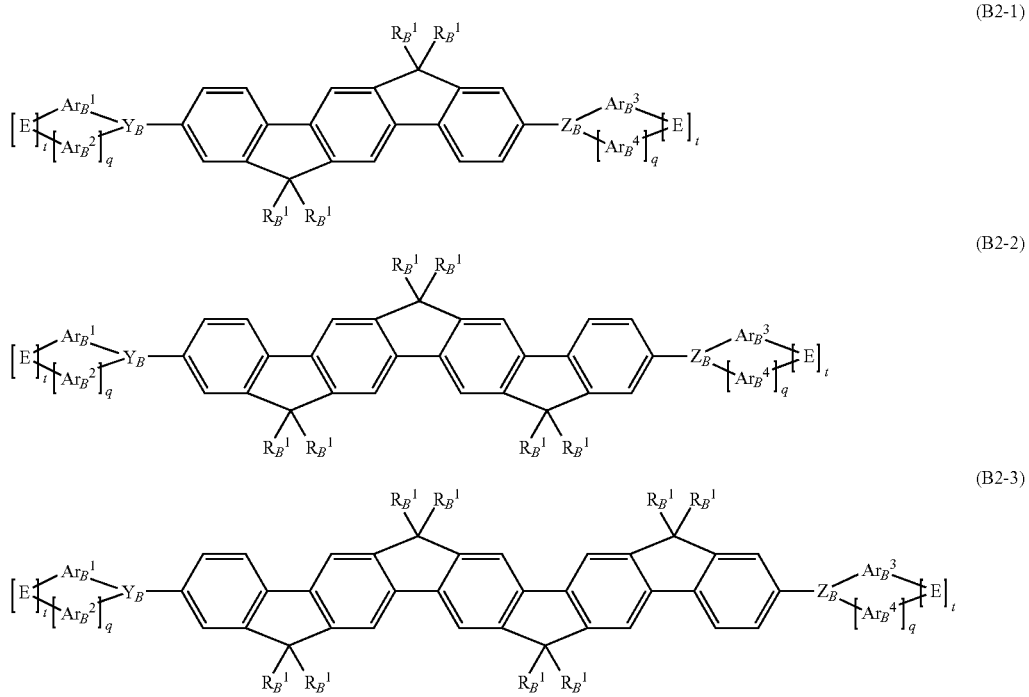

In the general formulae (B2-1), (B2-2), and (B2-3), Y$_B$, Z$_B$, Ar$_B^1$, Ar$_B^2$, Ar$_B^3$, Ar$_B^4$, E, R$_B^1$, q, r, and t have the same meanings as Y$_B$, Z$_B$, Ar$_B^1$, Ar$_B^2$, Ar$_B^3$, Ar$_B^4$, E, R$_B^1$, q, r, and t in the general formulae (B1-1), (B1-2), and (B1-3).

In the general formulae (B2-1), (B2-2), and (B2-3), the specific examples and the preferred examples of Y$_B$, Z$_B$, Ar$_B^1$, Ar$_B^2$, Ar$_B^3$, Ar$_B^4$, E, q, r, and t are the same as the specific examples and the preferred examples of Y$_B$, Z$_B$, Ar$_B^1$, Ar$_B^2$, Ar$_B^3$, Ar$_B^4$, E, q, r, and t in the general formulae (B1-1), (B1-2), and (B1-3).

In the general formulae (B2-1), (B2-2), and (B2-3), from the viewpoint of deposition suitability, the general formulae (B2-1) and (B2-2) are preferred, and the general formula (B2-1) is more preferred.

In the general formulae (B2-1), (B2-2), and (B2-3), the specific examples and the preferred examples of R$_B^1$, are the same as the specific examples and the preferred examples of R$_B^1$ in the general formulae (B1-1), (B1-2), and (B1-3), but R$_B^1$ is particularly preferably a linear alkyl group having 1 to 4 carbon atoms or an aryl group having 6 to 10 carbon atoms, more preferably a methyl group or a phenyl group, and still more preferably a methyl group. Two or more $R_B^1$ groups may be combined with each other to form a ring structure.

If a plurality of $R_B^1$ groups are combined with each other to form a ring structure, a spiro structure is formed. In particular, if the $R_B^1$ group is a phenyl group, the structure is a structure of the following general formula (B3-1), (B3-2), or (B3-3).

In the general formula (B3), $Y_B$, $Z_B$, $Ar_B^1$, $Ar_B^2$, $Ar_B^3$, $Ar_B^4$, E, q, r, and t have the same meanings as $Y_B$, $Z_B$, $Ar_B^1$, $Ar_B^2$, $Ar_B^3$, $Ar_B^4$, E, q, r, and t in the general formulae (B1-1), (B1-2), and (B1-3). Each of the spiro structures may be substituted with one or more non-aromatic $R_B^1$ groups.

Hereinbelow, specific examples of the compound represented by the general formula (B1-1), (B1-2), or (B1-3) are shown below, but are not limited thereto.

[Chem. 17]

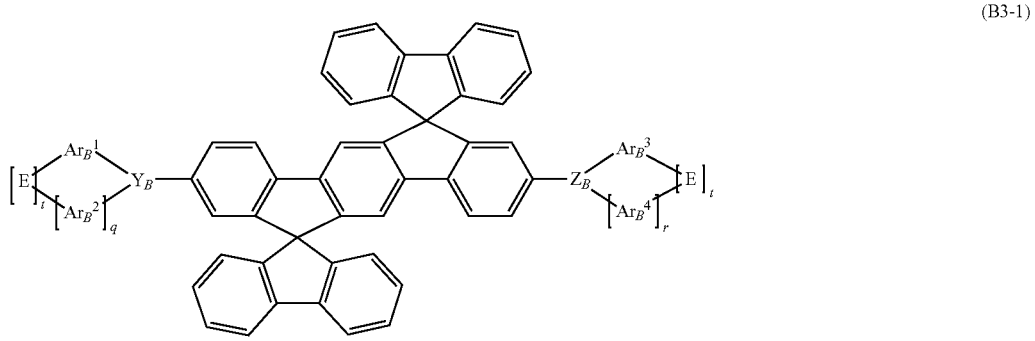

(B3-1)

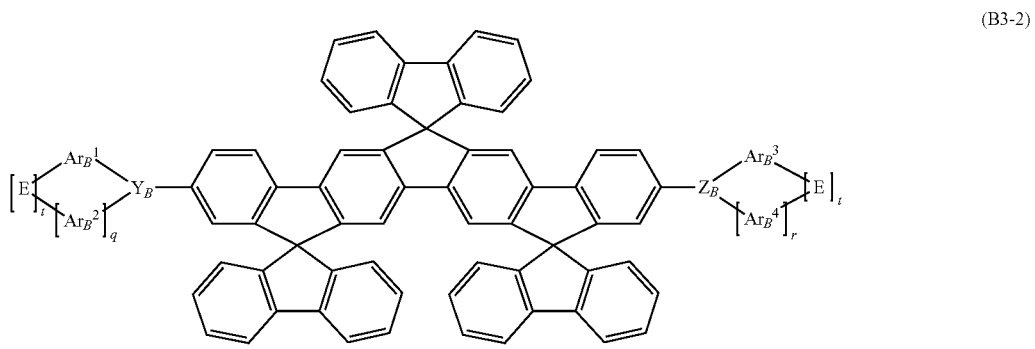

(B3-2)

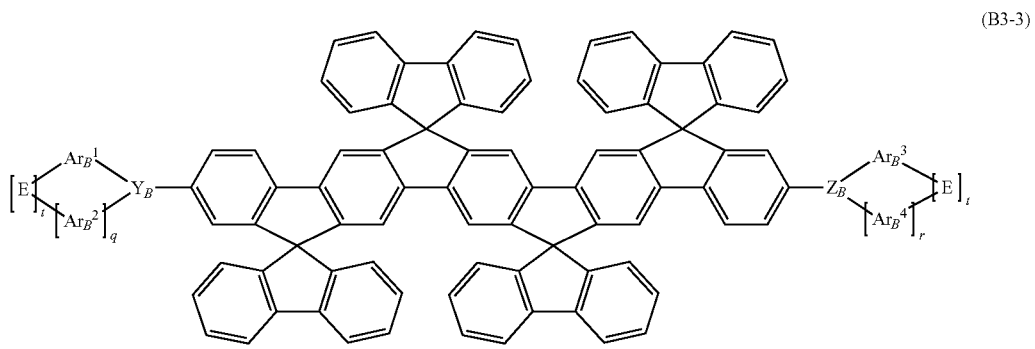

(B3-3)

[Chem. 18]
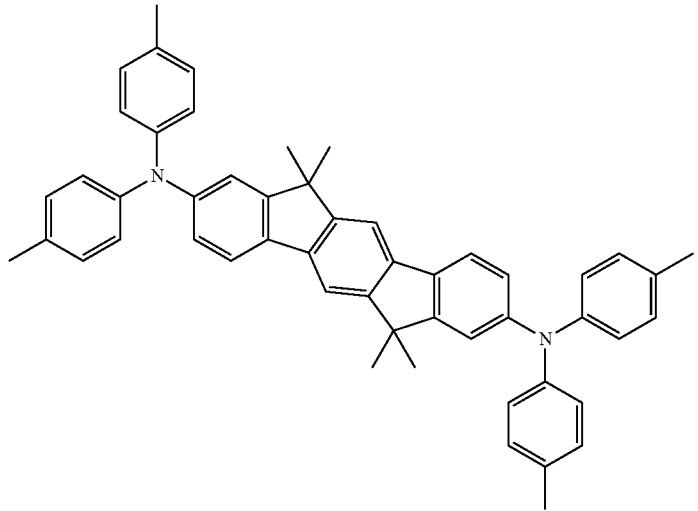
Compound 1
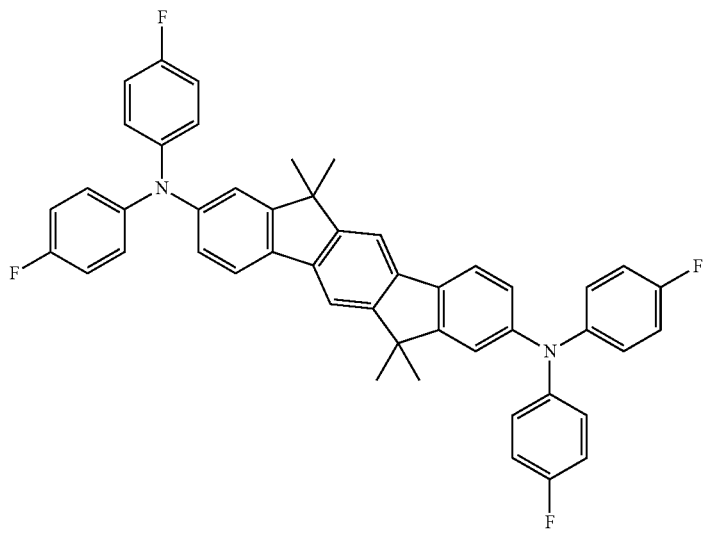
Compound 2
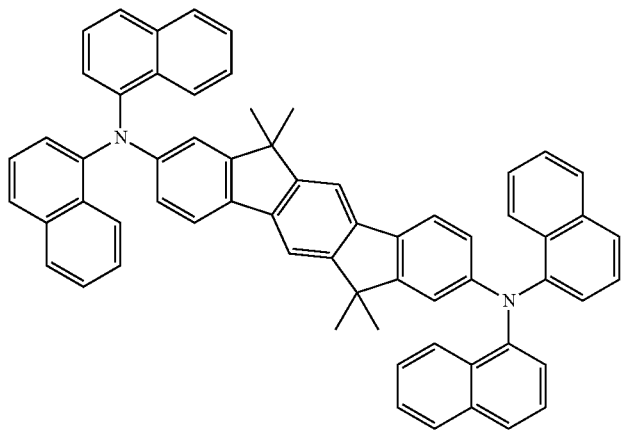
Compound 3

-continued
Compound 4
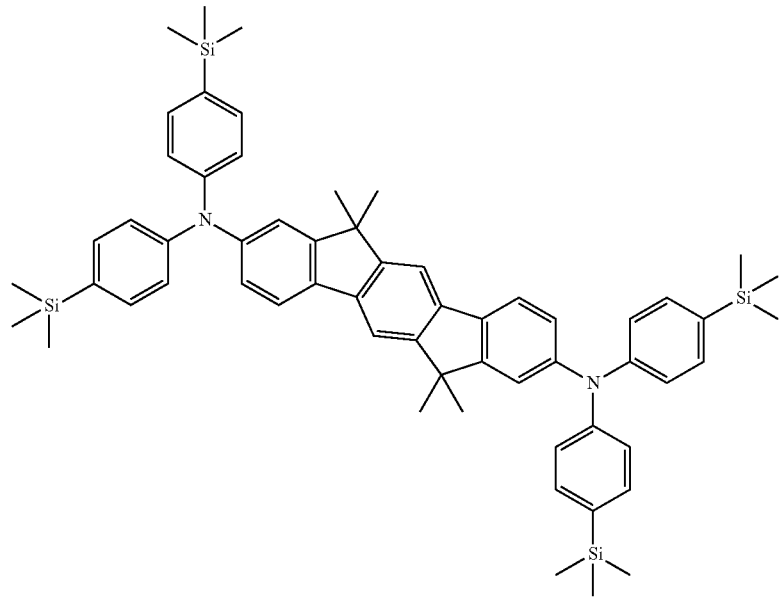
Compound 5
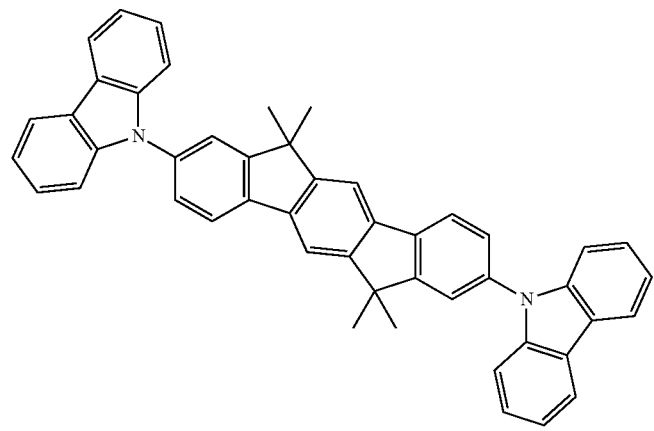
Compound 6
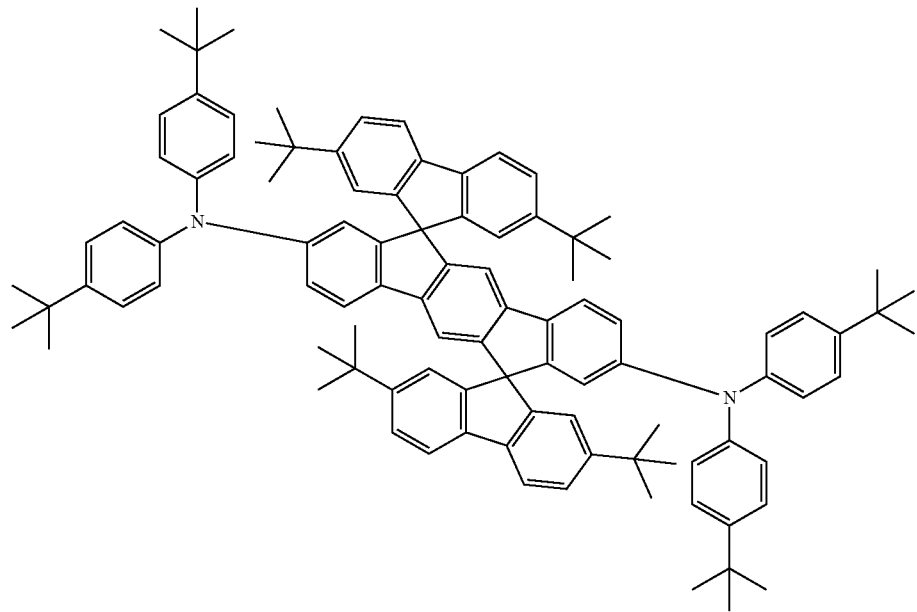

Compound 7
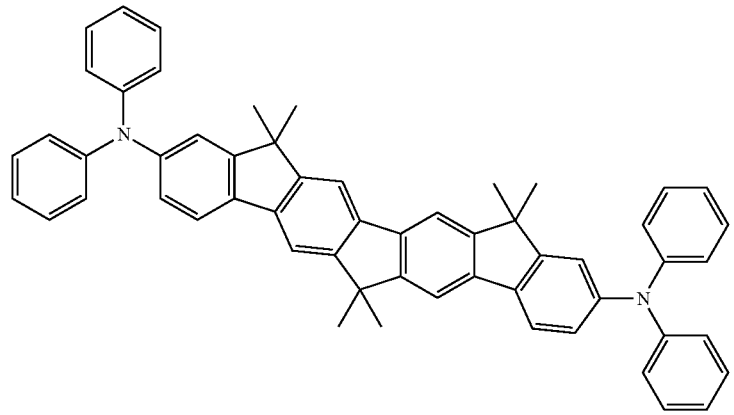
Compound 8
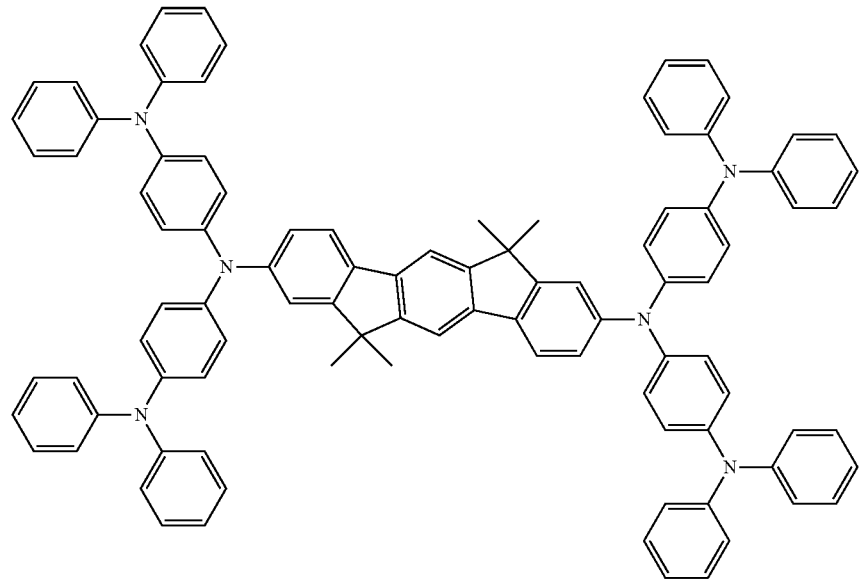
Compound 9
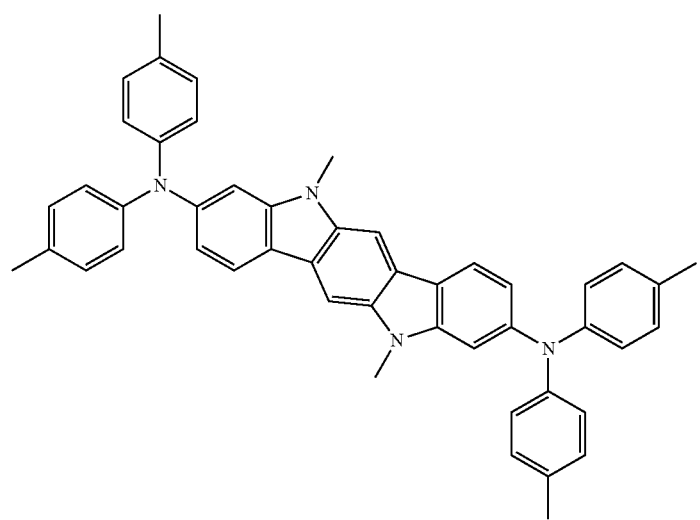

-continued

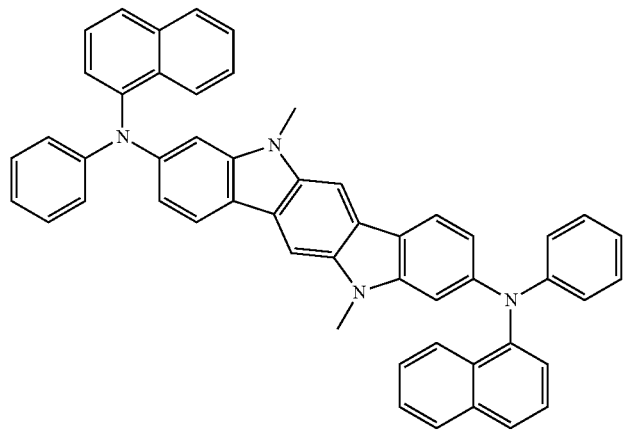

Compound 10

The compound according to the present invention can be used as, for example, a corresponding conjugated or partially non-conjugated polymer, a copolymer for preparation of an oligomer, or a core of a dendrimer. The polymerization is herein preferably implemented by a halogen functional group.

The compound according to the present invention can be synthesized by, for example, the method described in PTL 1.

In the present invention, the compound represented by the general formula (B1-1), (B1-2), or (B1-3) is contained in the light emitting layer as a light emitting material, but is not limited in its uses and may be further contained in any layer in the organic layers. Examples of the layer to which the compound represented by the general formula (B1-1), (B1-2), or (B1-3) is introduced include a hole injecting layer, a hole transporting layer, an electron transporting layer, an electron injecting layer, an exciton blocking layer, and a charge blocking layer, in addition to the light emitting layer, preferably an organic layer disposed between the light emitting layer and the anode, and more preferably a hole injecting layer and a hole transporting layer.

The compound represented by the general formula (B1-1), (B1-2), or (B1-3) is preferably contained in the amount of 0.1% by mass to 50% by mass, more preferably 1% by mass to 50% by mass, and still more preferably 2% by mass to 40% by mass, with respect to the total mass of the light emitting layer.

In the case where the compound represented by the general formula (B1-1), (B1-2), or (B1-3) is further contained in layers other than the light emitting layer, it is preferably contained in the amount of 1% by mass to 20% by mass, and more preferably 5% by mass to 15% by mass, with respect to the total mass of the layer.

[Organic Electroluminescent Element]

The organic electroluminescent element of the present invention is an organic electroluminescent element including a substrate, a pair of electrodes including an anode and a cathode, disposed on the substrate, a light emitting layer disposed between the electrodes, and at least one organic layer disposed between the light emitting layer and the anode, in which at least one kind of compound represented by the general formula (A) is contained in at least one organic layer disposed between the light emitting layer and the anode, and at least one kind of compound represented by the general formula (B1-1), (B1-2), or (B1-3) is contained as a light emitting material in the light emitting layer.

In the organic electroluminescent element of the present invention, the light emitting layer is an organic layer and at least one organic layer is included between the light emitting layer and the anode, but other organic layers may be further included.

In view of the properties of the light emitting element, at least one electrode of the anode and the cathode, is preferably transparent or semi-transparent. FIG. 1 shows one example of the configuration of the organic electroluminescent element according to the present invention. The organic electroluminescent element 10 according to the present invention in FIG. 1 has a light emitting layer 6 interposed between an anode 3 and a cathode 9 on a supporting substrate 2. Specifically, a hole injecting layer 4, a hole transporting layer 5, a light emitting layer 6, a hole blocking layer 7, and an electron transporting layer 8 are laminated in this order between the anode 3 and the cathode 9.

<Configuration of Organic Layer>

The layer configuration of the organic layer is not particularly limited and can be suitably selected depending on the use and purpose of the organic electroluminescent element. However, the organic layer is preferably formed on the transparent electrode or the rear electrode. In that case, the organic layer is formed on the entire surface or the partial surface of the transparent electrode or the rear electrode.

The shape, the size, the thickness, and the like of the organic layer are not particularly limited and can be suitably selected depending on the purpose.

Specific examples of the layer configuration include the following, but the present invention is not limited to these configurations.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injecting layer/cathode Anode/hole injecting layer/hole transporting layer/light emitting layer/electron transporting layer/electron injecting layer/cathode Anode/hole injecting layer/hole transporting layer/light emitting layer/blocking layer/electron transporting layer/cathode Anode/hole injecting layer/hole transporting layer/light emitting layer/blocking layer/electron transporting layer/electron injecting layer/cathode The element configuration, the substrate, the cathode, and the anode of the organic electroluminescent element are described in detail in, for example, JP-A-2008-270736, and the detailed descriptions in the publication can be applied to the present invention.

<Substrate>

The substrate used in the present invention is preferably a substrate that does not scatter or decay light emitted from the organic layer. In the case of an organic material, those having excellent heat resistance, dimensional stability, solvent resistance, electrical insulating properties, and processability are preferred.

<Anode>

The anode may be typically one having a function as an electrode of supplying holes into an organic layer, and is not particularly limited in its shape, structure, size, or the like. Further, depending on the use and purpose of the light emitting element, the anode can be suitably selected from the known electrode materials. As described above, the anode is usually provided as a transparent anode.

<Cathode>

The cathode may be typically one having a function as an electrode of injecting electrons to an organic layer, and is not particularly limited in its shape, structure, size, or the like. Further, depending on the use and purpose of the light emitting element, the cathode can be suitably selected from the known electrode materials.

For the substrate, the anode, and the cathode, the detailed descriptions in paragraph Nos. [0070] to [0089] of JP-A-2008-270736 can be applied to the present invention.

<Organic Layer>

The organic layer in the present invention will be described.

[Formation of Organic Layer]

The respective organic layers in the organic electroluminescent element of the present invention can be suitably formed by any of dry film forming methods such as a deposition method and a sputtering method, and solution coating processes such as a transfer method, a printing method, a spin coating method, and a bar coating method.

[Light Emitting Layer]

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting.

The substrate, the anode, the cathode, the organic layer, and the light emitting layer are described in detail in, for example, JP-A-2008-270736 and JP-A-2007-266458, and the detailed descriptions in these publications can be applied to the present invention. Further, the light emitting layer may include a material which does not have charge transporting properties and does not emit light.

As a light emitting material in the light emitting layer, the compound represented by the general formula (B1-1), (B1-2), or (B1-3) is contained. The light emitting material is generally contained in the amount of 0.1% by mass to 50% by mass with respect to the total mass of the light emitting layer-forming compounds in the light emitting layer, but from the viewpoints of durability and external quantum efficiency, it is preferably in the amount of 1% by mass to 50% by mass, and more preferably 2% by mass to 40% by mass.

The thickness of the light emitting layer is not particularly limited, but usually, it is preferably from 2 nm to 500 nm, and among these, from the viewpoint of external quantum efficiency, it is more preferably from 3 nm to 200 nm, still more preferably from 5 nm to 100 nm, and particularly preferably from 20 nm to 40 nm.

The light emitting layer in the element of the present invention may contain a light emitting material other than the compound represented by the general formula (B1-1), (B1-2), or (B1-3), in addition to the compound represented by the general formula (B1-1), (B1-2), or (B1-3). The light emitting material may be a fluorescent light emitting material or a phosphorescent light emitting material.

The light emitting layer in the element of the present invention is preferably configured to be a mixed layer formed with a light emitting material and a host material. The host material is preferably a charge transporting material. The host materials may be made of one kind or two or more kinds thereof, and may be configured to be, for example, a mixture of an electron transporting host material and a hole transporting host material. Further, the light emitting layer may include a material which does not have charge transporting properties and does not emit light.

In addition, the light emitting layer may be made of a single layer or multiple layers of two or more layers. Further, the respective light emitting layers may emit light in a different luminous color from each other.

<Host Material>

The host material used in the present invention may contain the following compound or a derivative of the following compound.

Examples of the host material include an electron transporting material and a hole transporting material, and preferably a charge transporting material. The host material may be made of one kind or two or more kinds thereof, and may be configured to be, for example, a mixture of an electron transporting host material and a hole transporting host material.

Examples of the host material include conductive high-molecular oligomers such as fluorene, pyrene, anthracene, pyrrole, indole, carbazole (for example, CBP (4,4'-di(9-carbazolyl)biphenyl), 3,3'-di(9-carbazolyl)biphenyl)), azaindole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, polysilane-based compounds, poly(N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring).

In the light emitting layer in the present invention, it is preferable that the singlet lowest excitation energy–($S_1$ energy) of the host material be higher than the $S_1$ energy of the light emitting material, in terms of color purity, luminous efficiency, and driving durability.

Moreover, the content of the host compound in the present invention is not particularly limited, but from the viewpoints of luminous efficiency and driving voltage, it is preferably from 15% by mass to 99.9% by mass, more preferably from 50% by mass to 99% by mass, and still more preferably from 50% by mass to 95% by mass, with respect to the total mass of the light emitting layer-forming compounds.

(Charge Transporting Layer)

The charge transporting layer refers to a layer in which charges move when voltage is applied to the organic electroluminescent element. Specific examples thereof include a hole injecting layer, a hole transporting layer, an electron blocking layer, a light emitting layer, a hole blocking layer, an electron transporting layer, and an electron injecting layer. The charge transporting layer is preferably a hole injecting layer, a hole transporting layer, an electron blocking layer, or a light emitting layer. When the charge transporting layer formed by a coating method is a hole injecting layer, a hole transporting layer, an electron blocking layer, or a light emitting layer, it becomes possible to prepare an organic electroluminescent element with low cost and high efficiency. Incidentally, the charge transporting layer is more preferably a hole injecting layer, a hole transporting layer, or an electron blocking layer.

(Hole Injecting Layer and Hole Transporting Layer)

The hole injecting layer and the hole transporting layer are layers having a function of receiving holes from the anode or the anode side and transporting them to the cathode side.

The hole injecting layer and the hole transporting layer are described in detail in, for example, JP-A-2008-270736 and JP-A-2007-266458, and the detailed descriptions in these publications can be applied to the present invention.

In addition, in the present invention, the compound represented by the general formula (B1-1), (B1-2), or (B1-3) is preferably contained in the hole injecting layer or the hole transporting layer. Further, the following compounds can also be used as a hole injecting material/a hole transporting material.

[Chem. 19]

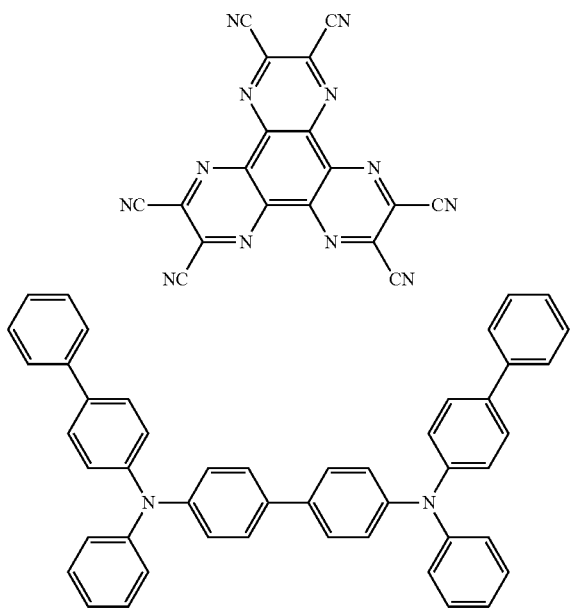

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from a material to be doped and generating radical cations, and examples thereof include tetracyanoquinodimethane (TCNQ), tetrafluorotetracyanoquinodimethane ($F_4$-TCNQ), and molybdenum oxide.

The electron receptive dopant in the hole injecting layer is contained in the amount of preferably from 0.1% by mass to 50% by mass, more preferably from 0.1% by mass to 40% by mass, and still more preferably from 0.5% by mass to 30% by mass, with respect to the total mass of the hole injecting layer-forming compounds.

(Electron Injecting Layer and Electron Transporting Layer)

The electron injecting layer and the electron transporting layer are layers having a function of receiving electrons from the cathode or the cathode side and transporting them to the anode side. The electron injecting material and the electron transporting material used in these layers may be low-molecular compounds or high-molecular compounds.

The electron injecting layer and the electron transporting layer are described in detail in, for example, JP-A-2008-270736 and JP-A-2007-266458, and the detailed descriptions in these publications can be applied to the present invention. The electron transporting layer is particularly preferably tris(8-quinolinolato)aluminum (Alq), an imidazole derivative, or the like, and more preferably an imidazole derivative.

The electron injecting layer preferably contains an electron donating dopant. By incorporating the electron donating dopant in the electron injecting layer, there are effects in which the electron injecting properties are improved, the driving voltage is lowered, and the efficiency is improved.

The electron donating dopant may be any one of an organic material and an inorganic material as long as it is capable of giving electrons to a material to be doped and generating radical anions, and examples thereof include tetrathiafulvalene (TTF), tetrathianaphthacene (TTT), lithium, and cesium.

The electron donating dopant in the electron injecting layer is contained in the amount of preferably from 0.1% by mass to 50% by mass, more preferably from 0.1% by mass to 40% by mass, and still more preferably 0.5% by mass to 30% by mass, with respect to the total mass of the electron injecting layer-forming compounds.

(Hole Blocking Layer)

The hole blocking layer is a layer having a function of preventing holes, which have been transported from the anode side to the light emitting layer, from passing through to the cathode side. In the present invention, the hole blocking layer can be provided as an organic layer adjacent to the light emitting layer and the cathode side.

Examples of the organic compounds constituting the hole blocking layer include aluminum complexes such as aluminum (III) bis(2-methyl-8-quinolinato) 4-phenylphenolate (abbreviated as BAlq), triazole derivatives, phenanthroline derivatives such as 2,9-dimethyl-4,7-diphenyl-1,10-phenanthroline (abbreviated as BCP), triphenylene derivatives, and carbazole derivatives.

The triphenylene derivatives are described in, for example, WO05/013388, WO06/130598, and WO09/021107.

The thickness of the hole blocking layer is preferably from 1 nm to 500 nm, more preferably from 5 nm to 200 nm, and still more preferably from 5 nm to 50 nm.

The hole blocking layer may have either a single layer structure composed of one kind or two or more kinds of the above-described materials or a multilayer structure composed of a plurality of layers having the same composition or different compositions.

(Electron Blocking Layer)

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer and the anode side.

As the organic compound constituting the electron blocking layer, for example, those exemplified above as the hole transporting material can be applied.

The thickness of the electron blocking layer is preferably from 1 nm to 500 nm, more preferably from 5 nm to 200 nm, and still more preferably from 10 nm to 100 nm.

The electron blocking layer may have either a single layer structure composed of one kind or two or more kinds of the above-described materials or a multilayer structure composed of a plurality of layers having the same composition or different compositions.

(Protective Layer)

In the present invention, the entirety of the organic EL element may be protected by a protective layer.

The material included in the protective layer may be any one having a function of inhibiting substances that promotes the deterioration of the element, such as moisture and oxygen, from entering the element.

For the protective layer, the detailed descriptions in paragraph Nos. [0169] to [0170] of JP-A-2008-270736 can be applied to the present invention.

(Sealing Enclosure)

For the element according to the present invention, the entirety of the element may be sealed using a sealing enclosure.

For the sealing enclosure, the detailed descriptions in paragraph No. [0171] of JP-A-2008-270736 can be applied to the present invention.

In addition, a moisture absorbent or an inert liquid may be enclosed in the space between the sealing enclosure and the light emitting element. The moisture absorbent is not particularly limited, but examples thereof include barium oxide, sodium oxide, potassium oxide, calcium oxide, sodium sulfate, calcium sulfate, magnesium sulfate, phosphorous pentaoxide, calcium chloride, magnesium chloride, copper chloride, cesium fluoride, niobium fluoride, calcium bromide, vanadium bromide, molecular sieves, zeolite, and magnesium oxide. The inert liquid is not particularly limited, but examples thereof include paraffins, fluidized paraffins, perfluoroalkanes or perfluoroamine, fluorine-based solvents such as perfluoroether, chlorine-based solvents, and silicone oils.

(Driving)

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. The light extraction efficiency in usual organic EL elements is about 20%, but by taking into consideration the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

The organic electroluminescent element of the present invention has a highest light emitting wavelength (maximum intensity wavelength of the luminous spectrum) of preferably from 350 nm to 700 nm, more preferably from 350 nm to 600 nm, still more preferably from 400 nm to 520 nm, and particularly preferably from 400 nm to 465 nm.

<Use of Light Emitting Element of the Present Invention>

The light emitting element of the present invention can be suitably used for light emitting devices, pixels, display elements, displays, backlights, electrophotography, illumination light sources, recording light sources, exposure light sources, readout light sources, signs, billboards, interior decorations, optical communications, and the like, and in particular, devices driven in a region of high-intensity luminescence, such as an illumination device and a display device.

(Light Emitting Device)

Next, the light emitting device of the present invention will be described with reference to FIG. 2.

The light emitting device of the present invention is formed by using the organic electroluminescent element.

Figure 2:
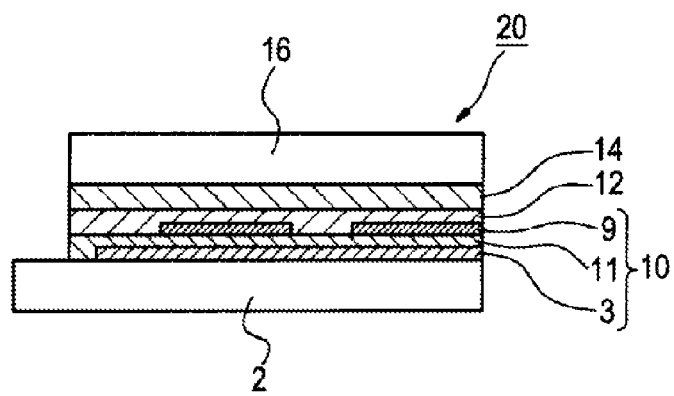
FIG. 2 is a schematic view showing one example of a light emitting device according to the present invention.

FIG. 2 is a cross-sectional view schematically showing one example of the light emitting device of the present invention.

The light emitting device 20 in FIG. 2 includes a substrate (supporting substrate) 2, an organic electroluminescent element 10, a sealing enclosure 16, and the like.

The organic electroluminescent element 10 is formed by laminating an anode (first electrode) 3, an organic layer 11, and a cathode (second electrode) 9 in this order on a substrate 2. In addition, a protective layer 12 is laminated on the cathode 9, and a sealing enclosure 16 is further provided via an adhesive layer 14 on the protective layer 12. Incidentally, a part of each of the electrodes 3 and 9, a diaphragm, an insulating layer, and the like are omitted.

Here, as the adhesive layer 14, a photocurable adhesive such as an epoxy resin, or a thermosetting adhesive can be used, and for example, a thermosetting adhesive sheet may also be used.

The light emitting device of the present invention is not particularly limited in its use, and it can be used as not only an illumination device but also a display device of a television set, a personal computer, a mobile phone, electronic paper, or the like.

(Illumination Device)

Next, the illumination device according to one embodiment of the present invention will be described with reference to FIG. 3.

Figure 3:
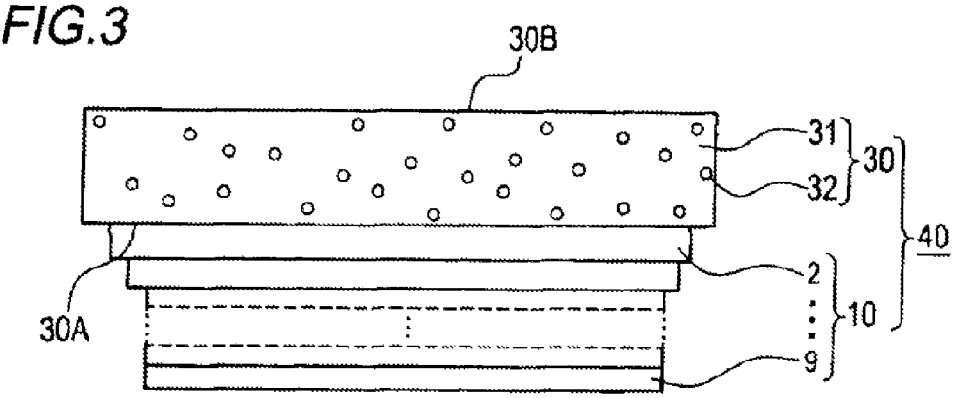
FIG. 3 is a schematic view showing one example of an illumination device according to the present invention.

FIG. 3 is a cross-sectional view schematically showing one example of the illumination device according to an embodiment of the present invention. The illumination device 40 according to an embodiment of the present invention includes, as shown in FIG. 3, the above-described organic EL element 10 and a light scattering member 30.

More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. A suitable example of the transparent substrate 31 is a glass substrate, and suitable examples of the fine particles 32 include transparent resin fine particles. As the glass substrate and the transparent resin fine particles, a known product can be used for both of them. In such an illumination device 40, when light emitted from the organic electroluminescent element 10 is incident on the light incident surface 30A of the light scattering member 30, the incident light is scattered by the light scattering member 30 and the scattered light is output as illuminating light from the light outputting surface 30B.

EXAMPLES

Hereinbelow, the present invention will be described in more detail with reference to Examples, but the present invention is not limited thereto.

Synthesis Example 1

Furthermore, as the organic material used in the present Example, any products subjected to sublimation purification are used and analyzed by high performance liquid chromatography (TSKgel ODS-100Z manufactured by Tosoh Corporation), and thus, ones having an absorption intensity area ratio at 254 nm of 99.9% or more were used.

Example 1

Fabrication of Organic Electroluminescent Element

An indium tin oxide (ITO) transparent conductive film was deposited on a glass substrate to give a thickness of 100 nm and patterned (manufactured by Geomatec Co., Ltd.), which was used as an anode. The ITO substrate was subjected to ultrasonic cleaning with acetone, rinsing with pure water, and ultrasonic cleaning with isopropyl alcohol in this order, then dried by blowing nitrogen, finally subjected to ultraviolet-ozone cleaning, and placed in a vacuum deposition device to evacuate until a degree of vacuum inside the deposition device decreased to $2.7 \times 10^{-4}$ Pa or less.

Subsequently, HATCN was heated in the vacuum deposition device to form a hole injecting layer having a film thickness of 10 nm.

A layer of the organic material was formed by a method in which an organic material was put into a crucible, the crucible was placed on filaments, and evacuated, and then the filaments were heated.

Here, a compound 1 was placed into the crucible in advance and heated by a heater to form a first hole transporting layer having a film thickness of 20 nm on the hole injecting layer as formed above.

Subsequently, HTM1 was heated by a heater to form a second hole transporting layer having a film thickness of 20 nm on the first hole transporting layer as formed above.

Furthermore, on the second hole transporting layer thus formed, Host A as a host material contained in the light emitting layer and the compound 1 as a light emitting material were heated simultaneously, thereby forming a light emitting layer. The deposition rate was controlled to adjust the content of the compound 1 to 5% by mass with respect to the entire light emitting layer, thereby laminating a light emitting layer having a film thickness of 30 nm on the second hole transporting layer.

Lastly, Alq was deposited to laminate an electron transporting layer having a film thickness of 20 nm on the light emitting layer.

Lithium fluoride (LiF) was then formed as a film on the electron transporting layer to give a film thickness of 1 nm by deposition, thereby forming an electron injecting layer.

Further, aluminum was further formed as a film thereon by deposition to give a film thickness of 100 nm, thereby forming a cathode.

The layer configuration of the element in Example 1 is shown below.

| | | |
|---|---|---|
| (Cathode) | aluminum | |
| (Electron injecting layer) | LiF | Film thickness 1 nm |
| (Electron transporting layer) | Alq | Film thickness 20 nm |
| (Light emitting layer) | Host A: compound 1 (mass ratio 95:5) | Film thickness 30 nm |
| (Second hole transporting layer) | HTM1 | Film thickness 20 nm |
| (First hole transporting layer) | compound 1 | Film thickness 20 nm |
| (Hole injecting layer) | HATCN | Film thickness 10 nm |
| (Anode) | ITO | |
| Glass substrate | | |

Examples 2 to 29 and Comparative Examples 1 to 12

In the same manner as in Example 1 except that the materials used, the use ratios, and the film thickness for the second hole transporting layer, light emitting layer, and electron transporting layer were changed to the film thickness as shown in Tables 1 to 4 in Example 1, organic electroluminescent light emitting elements in Examples 2 to 29 and Comparative Examples 1 to 12 were fabricated.

(Evaluation)

The organic electroluminescent element in Example 1 as fabricated above was allowed to emit light using BM-8 manufactured by Topcon Corporation to 2,000 cd/m², and was continuously driven at a current value at the above moment. The time (hours) taken until the luminance was lowered to 90% (T90) and the time (hours) taken until the luminance was lowered to 50% (T50) were evaluated. For the other elements, the spectrum was measured using SR-3 manufactured by Topcon Corporation, the luminance corresponding to the same number of photons as the luminance when light was emitted with the element in Example 1 at 2,000 cd/m² was determined. Further, the current value was adjusted to the luminance using BM-8, and T90 and T50 were evaluated in the same manner as for the element in Example 1.

TABLE 1

| | Hole injecting layer | First hole transporting layer | Second hole transporting layer | Light emitting layer | Electron transporting layer | T90 | T50 |
|---|---|---|---|---|---|---|---|
| Example 1 | HATCN 10 nm | Compound 1 20 nm | HTM1 20 nm | Host A:compound 1 (95:5) 30 nm | Alq 20 nm | 220 | 2590 |
| Comparative Example 1 | HATCN 10 nm | Compound 1 20 nm | NPD 20 nm | Host A:compound 1 (95:5) 30 nm | Alq 20 nm | 65 | 2120 |
| Example 2 | HATCN 10 nm | Compound 1 20 nm | HTM1 20 nm | Host A:compound 2 (95:5) 30 nm | Alq 20 nm | 181 | 2340 |
| Example 3 | HATCN 10 nm | Compound 1 20 nm | HTM1 20 nm | Host A:compound 3 (95:5) 30 nm | Alq 20 nm | 211 | 2520 |
| Example 4 | HATCN 10 nm | Compound 1 20 nm | HTM1 20 nm | Host A:compound 4 (95:5) 30 nm | Alq 20 nm | 198 | 2320 |
| Example 5 | HATCN 10 nm | Compound 1 20 nm | HTM1 20 nm | Host A:compound 5 (95:5) 30 nm | Alq 20 nm | 195 | 2450 |
| Example 6 | HATCN 10 nm | Compound 1 20 nm | HTM1 20 nm | Host A:compound 6 (95:5) 30 nm | Alq 20 nm | 190 | 2380 |
| Example 7 | HATCN 10 nm | Compound 1 20 nm | HTM1 20 nm | Host A:compound 7 (95:5) 30 nm | Alq 20 nm | 189 | 2470 |
| Example 8 | HATCN 10 nm | Compound 1 20 nm | HTM1 20 nm | Host A:compound 8 (95:5) 30 nm | Alq 20 nm | 190 | 2500 |
| Example 9 | HATCN 10 nm | Compound 1 20 nm | HTM1 20 nm | Host A:compound 9 (95:5) 30 nm | Alq 20 nm | 145 | 2350 |
| Example 10 | HATCN 10 nm | Compound 1 20 nm | HTM1 20 nm | Host A:compound 10 (95:5) 30 nm | Alq 20 nm | 138 | 2340 |
| Comparative Example 2 | HATCN 10 nm | Compound 1 20 nm | HTM1 20 nm | Host A:compound 11 (95:5) 30 nm | Alq 20 nm | 75 | 2400 |
| Comparative Example 3 | HATCN 10 nm | Compound 1 20 nm | HTM1 20 nm | Host A:compound 12 (95:5) 30 nm | Alq 20 nm | 71 | 2430 |

TABLE 2

| | Hole injecting layer | First hole transporting layer | Second hole transporting layer | Light emitting layer | Electron transporting layer | T90 | T50 |
|---|---|---|---|---|---|---|---|
| Example 11 | HATCN 10 nm | Compound 1 20 nm | HTM2 20 nm | Host A:compound 1 (95:5) 30 nm | Alq 20 nm | 215 | 2550 |
| Example 12 | HATCN 10 nm | Compound 1 20 nm | HTM3 20 nm | Host A:compound 1 (95:5) 30 nm | Alq 20 nm | 205 | 2570 |
| Example 13 | HATCN 10 nm | Compound 1 20 nm | HTM4 20 nm | Host A:compound 1 (95:5) 30 nm | Alq 20 nm | 210 | 2500 |
| Example 14 | HATCN 10 nm | Compound 1 20 nm | HTM5 20 nm | Host A:compound 1 (95:5) 30 nm | Alq 20 nm | 200 | 2450 |
| Example 15 | HATCN 10 nm | Compound 1 20 nm | HTM6 20 nm | Host A:compound 1 (95:5) 30 nm | Alq 20 nm | 150 | 2340 |
| Example 16 | HATCN 10 nm | Compound 1 20 nm | HTM7 20 nm | Host A:compound 1 (95:5) 30 nm | Alq 20 nm | 143 | 2320 |
| Comparative Example 4 | HATCN 10 nm | Compound 1 20 nm | HTM8 20 nm | Host A:compound 1 (95:5) 30 nm | Alq 20 nm | 80 | 2350 |

TABLE 3

| | Hole injecting layer | First hole transporting layer | Second hole transporting layer | Light emitting layer | Electron transporting layer | T90 | T50 |
|---|---|---|---|---|---|---|---|
| Example 17 | HATCN 10 nm | Compound 1 20 nm | HTM1 20 nm | Host A:compound 1 (90:10) 30 nm | Alq 20 nm | 210 | 2500 |
| Example 18 | HATCN 10 nm | Compound 1 20 nm | HTM1 20 nm | Host A:compound 1 (85:15) 30 nm | Alq 20 nm | 200 | 2450 |
| Example 19 | HATCN 10 nm | Compound 1 20 nm | HTM1 20 nm | Host A:compound 1 (99:1) 30 nm | Alq 20 nm | 155 | 2350 |
| Example 20 | HATCN 10 nm | Compound 1 20 nm | HTM1 20 nm | Host A:compound 1 (80:20) 30 nm | Alq 20 nm | 165 | 2320 |
| Example 21 | HATCN 10 nm | Compound 1 20 nm | HTM1 20 nm | Host A:compound 1 (95:5) 15nm | Alq 20 nm | 165 | 2200 |
| Example 22 | HATCN 10 nm | Compound 1 20 nm | HTM1 20 nm | Host A:compound 1 (95:5) 20 nm | Alq 20 nm | 200 | 2470 |

TABLE 3-continued

| | Hole injecting layer | First hole transporting layer | Second hole transporting layer | Light emitting layer | Electron transporting layer | T90 | T50 |
|---|---|---|---|---|---|---|---|
| Example 23 | HATCN 10 nm | Compound 1 20 nm | HTM1 20 nm | Host A:compound 1 (95:5) 40 nm | Alq 20 nm | 230 | 2620 |
| Example 24 | HATCN 10 nm | Compound 1 20 nm | HTM1 20 nm | Host A:compound 1 (95:5) 50 nm | Alq 20 nm | 170 | 2520 |

TABLE 4

| | Hole injecting layer | First hole transporting layer | Second hole transporting layer | Light emitting layer | Electron transporting layer | T90 | T50 |
|---|---|---|---|---|---|---|---|
| Example 25 | HATCN 10 nm | Compound 1 20 nm | HTM1 20 nm | Host A:compound 1 (95:5) 30 nm | ETM-1 20 nm | 235 | 3010 |
| Example 26 | HATCN 10 nm | Compound 1 20 nm | HTM1 20 nm | Host A:compound 1 (95:5) 30 nm | ETM-2 20 nm | 245 | 3150 |
| Example 27 | HATCN 10 nm | Compound 1 20 nm | HTM1 20 nm | Host A:compound 1 (95:5) 30 nm | ETM-3 20 nm | 225 | 2980 |
| Comparative Example 5 | HATCN 10 nm | Compound 1 20 nm | HTM8 20 nm | Host A:compound 1 (95:5) 30 nm | ETM-1 20 nm | 85 | 3020 |
| Comparative Example 6 | HATCN 10 nm | Compound 1 20 nm | HTM8 20 nm | Host A:compound 1 (95:5) 30 nm | ETM-2 20 nm | 90 | 2950 |
| Comparative Example 7 | HATCN 10 nm | Compound 1 20 nm | HTM8 20 nm | Host A:compound 1 (95:5) 30 nm | ETM-3 20 nm | 88 | 2960 |
| Comparative Example 8 | HATCN 10 nm | Compound 1 20 nm | HTM1 20 nm | Host A:compound 11 (95:5) 30 nm | ETM-1 20 nm | 86 | 2930 |
| Comparative Example 9 | HATCN 10 nm | Compound 1 20 nm | HTM1 20 nm | Host A:compound 11 (95:5) 30 nm | ETM-2 20 nm | 83 | 2980 |
| Comparative Example 10 | HATCN 10 nm | Compound 1 20 nm | HTM1 20 nm | Host A:compound 11 (95:5) 30 nm | ETM-3 20 nm | 89 | 3010 |
| Example 28 | HATCN 10 nm | Compound 1 20 nm | HTM1 20 nm | Host A:compound 1 (95:5) 30 nm | Alq 20 nm | 215 | 2480 |
| Example 29 | HATCN 10 nm | Compound 1 20 nm | HTM1 20 nm | Host A:compound 3 (95:5) 30 nm | Alq 20 nm | 210 | 2440 |
| Comparative Example 11 | HATCN 10 nm | Compound 1 20 nm | HTM1 20 nm | Host A:compound 11 (95:5) 30 nm | Alq 20 nm | 75 | 2420 |
| Comparative Example 12 | HATCN 10 nm | Compound 1 20 nm | HTM1 20 nm | Host A:compound 12 (95:5) 30 nm | Alq 20 nm | 72 | 2430 |

From the results of Tables 1 to 4, it can be seen that the elements of Examples have a longer initial drop time than the elements of Comparative Examples.

The compounds used in Examples and Comparative Examples are shown below.

[Chem. 20]

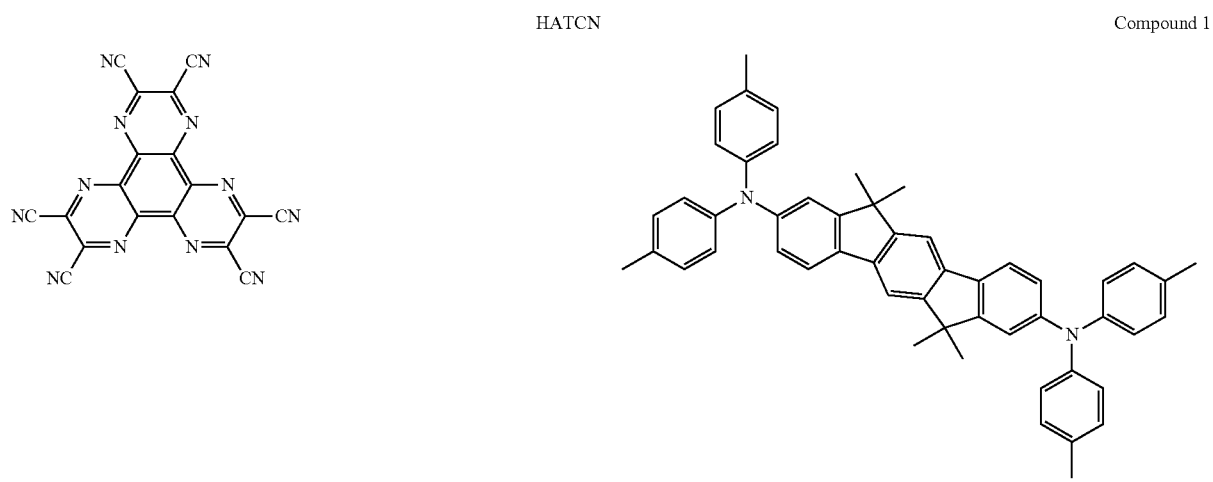

HATCN                    Compound 1

-continued
HTM1
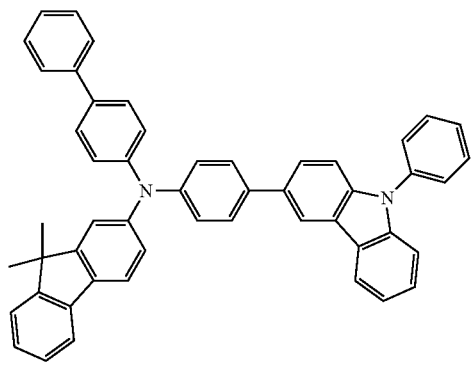
HostA
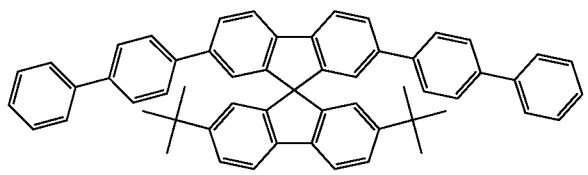
Alq
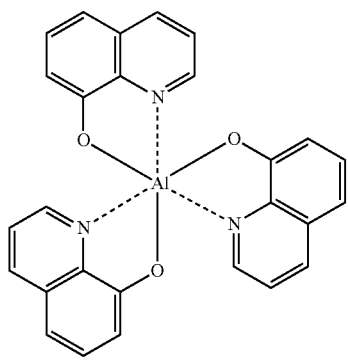
NPD
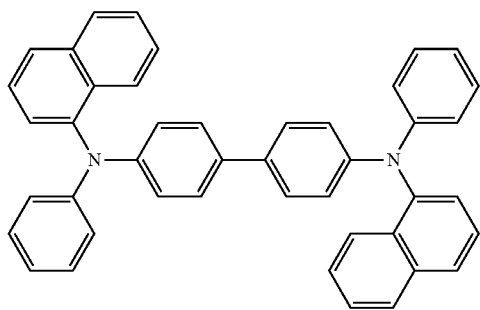
[Chem. 21]
Compound 2
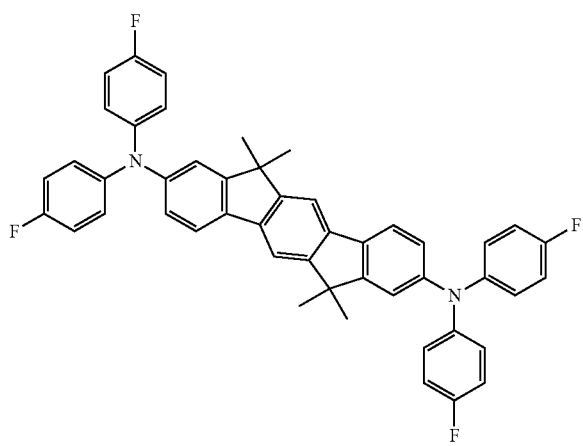
Compound 3
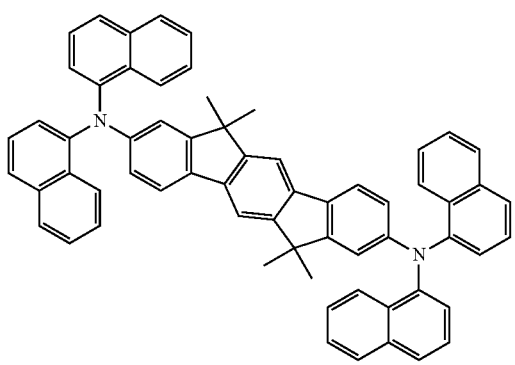

Compound 4
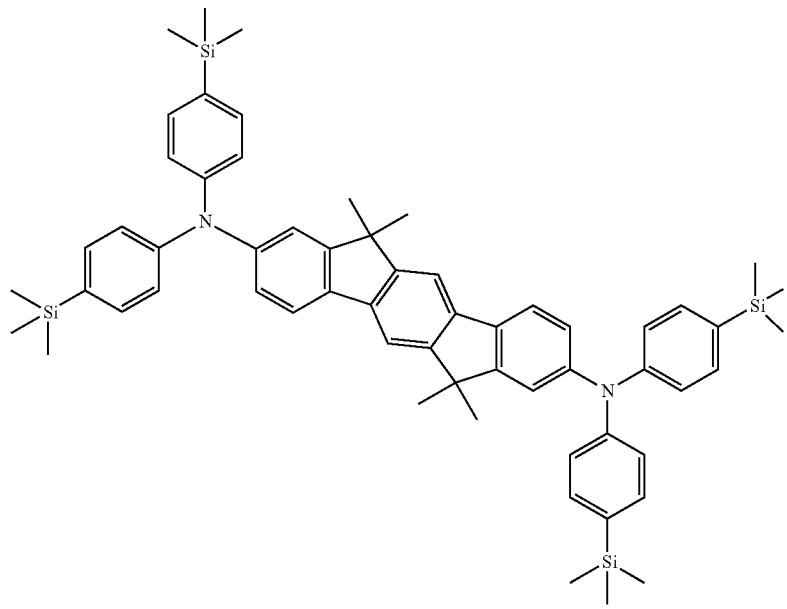
Compound 5
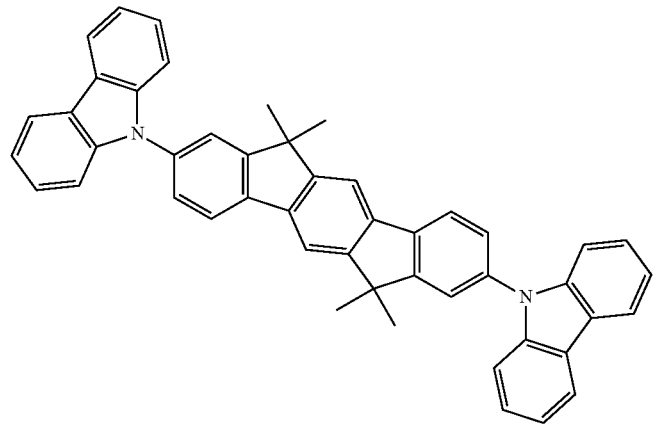
Compound 6
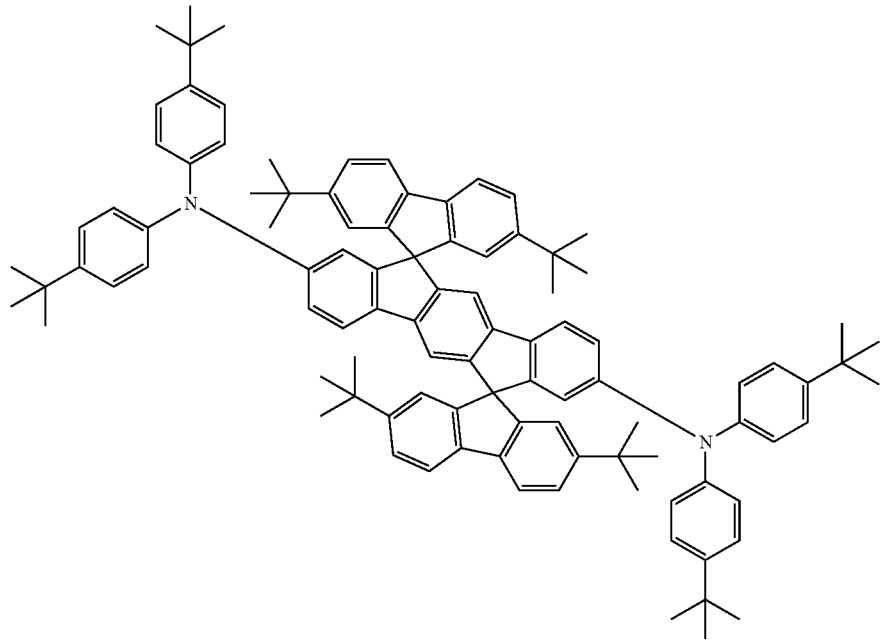

-continued
Compound 7
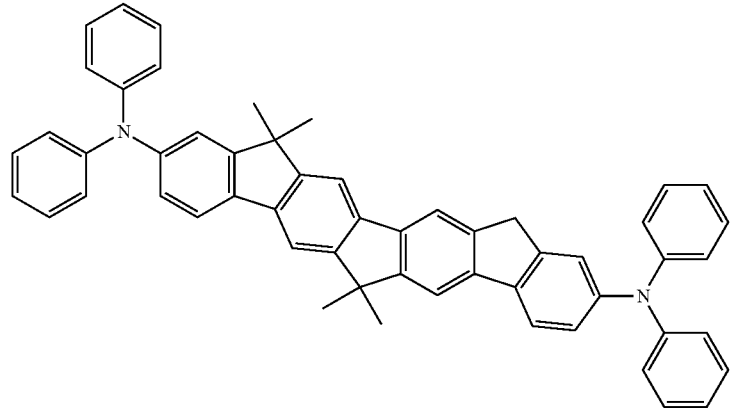
Compound 8
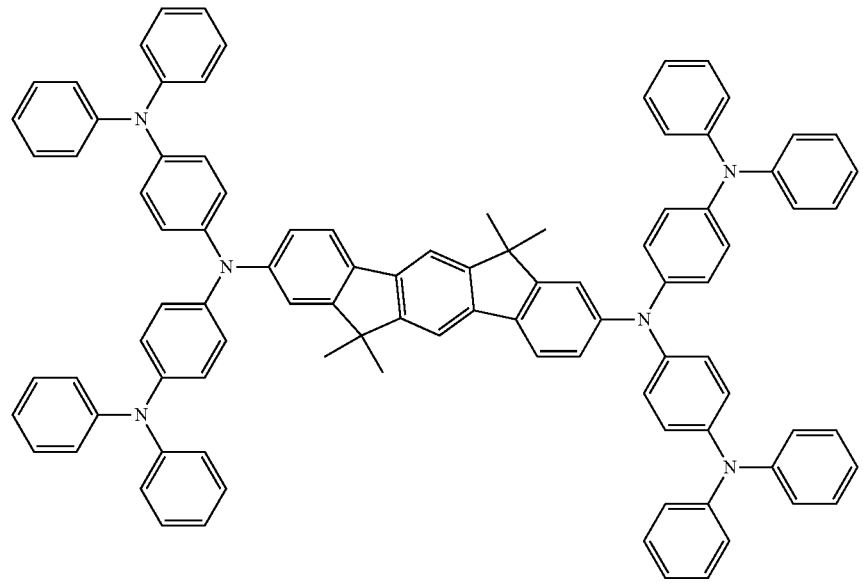
Compound 9
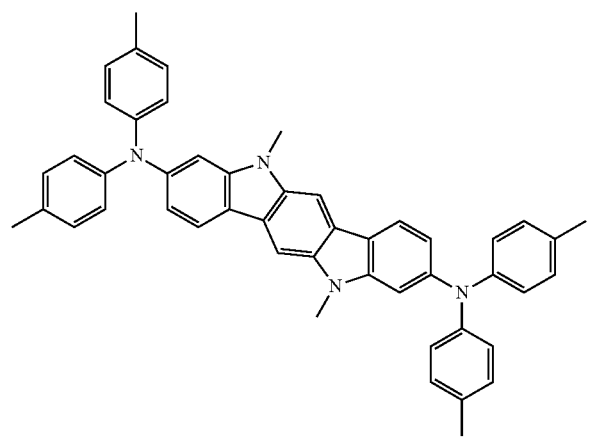
Compound 10
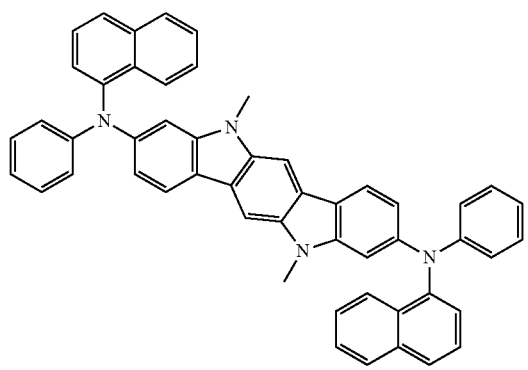

[Chem. 22]
HTM2
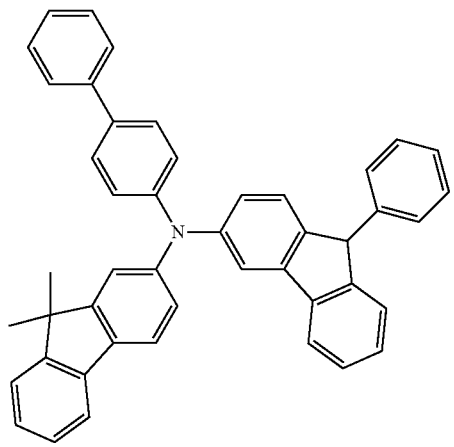
HTM3
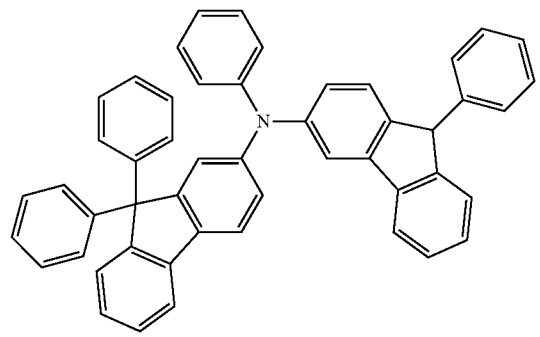
HTM4
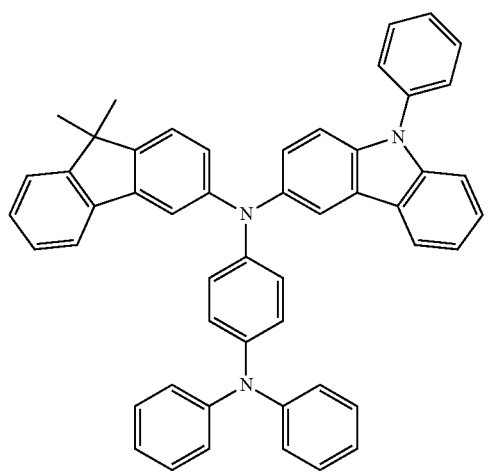
HTM5
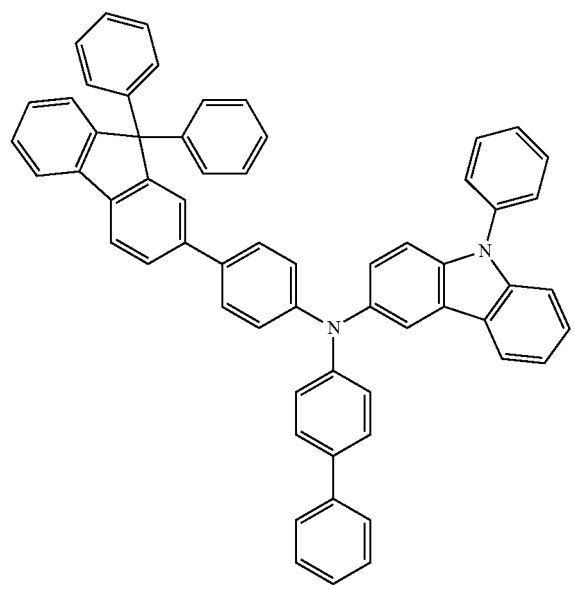
HTM6
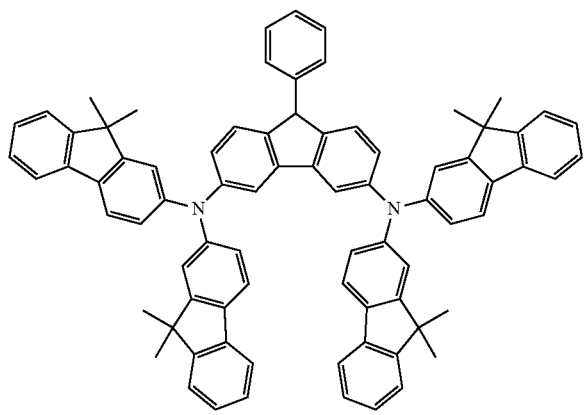
HTM7
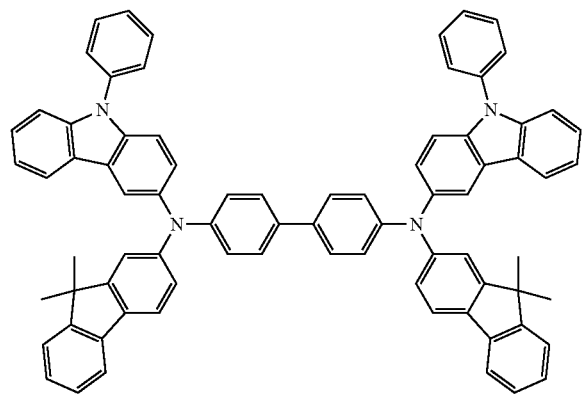

-continued
HTM8
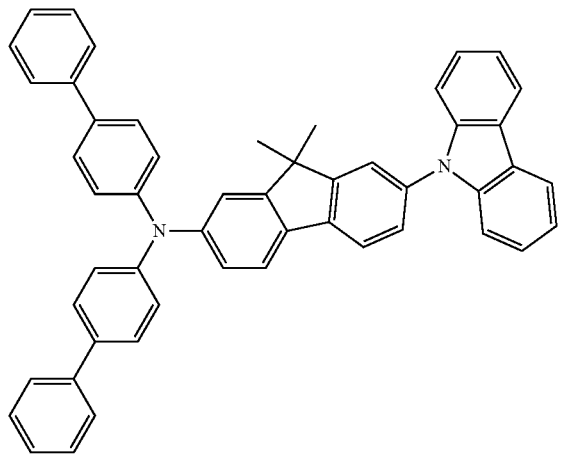
[Chem. 23]
Compound 11
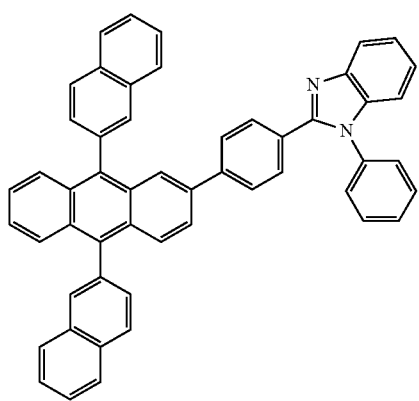
Compound 12
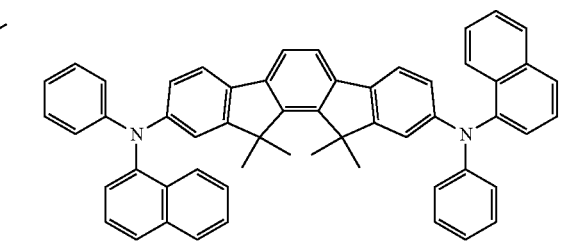
ETM-1
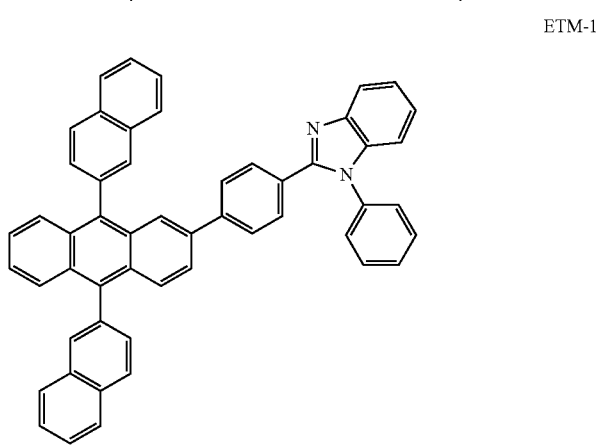
ETM-2
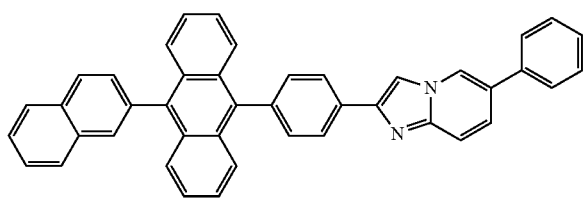
ETM-3
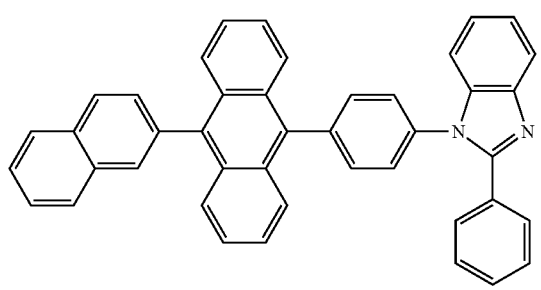
HostB
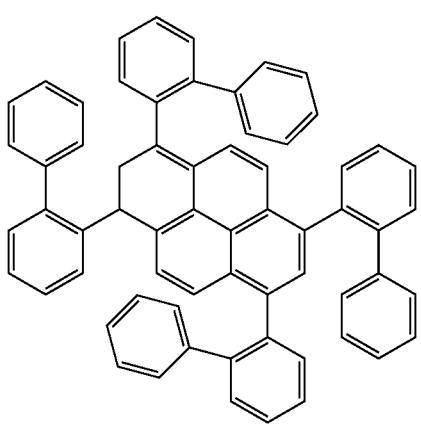

INDUSTRIAL APPLICABILITY

According to the present invention, an organic electroluminescent element having a small initial drop in the driving durability can be provided.

The present invention is described above in detail and with reference to specific embodiments, but various changes and modifications will be apparent to persons skilled in the art without departing from the spirit and scope of the present invention.

The present application is based on Japanese Patent Application No. 2011-218508 filed on Sep. 30, 2011, the contents of which are incorporated herein by reference.

REFERENCE SIGNS LIST

2: SUBSTRATE
3: ANODE
4: HOLE INJECTING LAYER
5: HOLE TRANSPORTING LAYER
6: LIGHT EMITTING LAYER
7: HOLE BLOCKING LAYER
8: ELECTRON TRANSPORTING LAYER
9: CATHODE
10: ORGANIC ELECTROLUMINESCENT ELEMENT
11: ORGANIC LAYER
12: PROTECTIVE LAYER
14: ADHESIVE LAYER
16: SEALING ENCLOSURE
20: LIGHT EMITTING DEVICE
30: LIGHT SCATTERING MEMBER
31: TRANSPARENT SUBSTRATE
30A: LIGHT INCIDENT SURFACE
30B: LIGHT OUTPUTTING SURFACE
32: FINE PARTICLES
40: ILLUMINATION DEVICE

The invention claimed is:
1. An organic electroluminescent element comprising:
a substrate;
a pair of electrodes including an anode and a cathode, disposed on the substrate;
a light emitting layer disposed between the electrodes; and
at least one organic layer disposed between the light emitting layer and the anode,
wherein at least one kind of compound represented by the following general formula (A) is contained in at least one organic layer disposed between the light emitting layer and the anode, and
at least one kind of compound represented by the following general formula (B1-1), (B1-2), or (B1-3) is contained as a light emitting material in the light emitting layer;

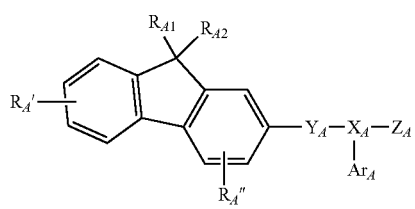

(A)

$Z_A$ represents a group of any one kind selected from the following general formulae (Za-1), (Za-2), and (Za-3);

In the following general formula (Za-1), (Za-2), or (Za-3); * represents a binding site to $X_A$ in the general formula (A);

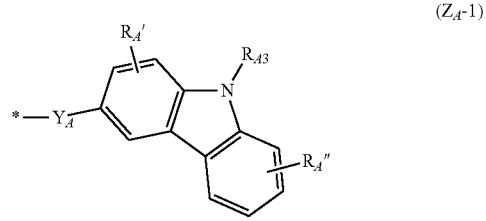

(Z$_A$-1)

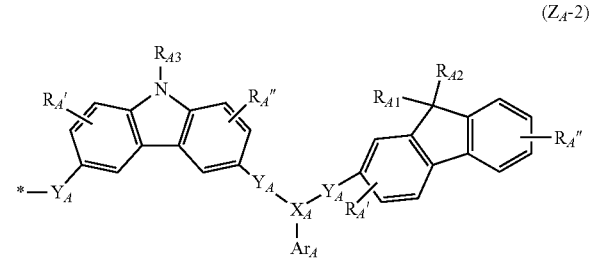

(Z$_A$-2)

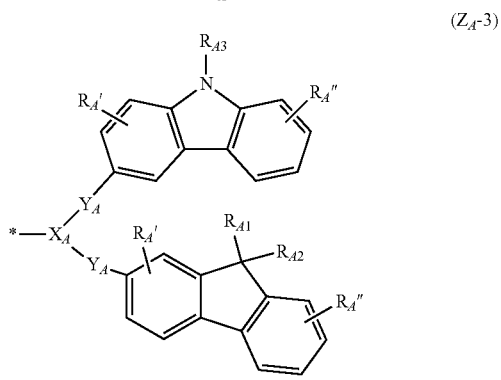

(Z$_A$-3)

wherein $Ar_A$'s are each independently a substituted or unsubstituted aryl group, a substituted or unsubstituted heteroaryl group, or a group represented by the following general formula ($Ar_A$-1), wherein * represents a binding site to $X_A$;

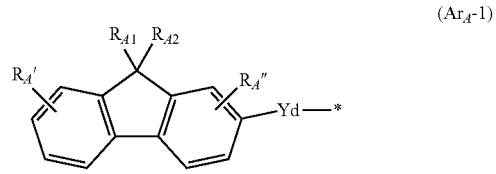

($Ar_A$-1)

where in the general formulae (A), ($Z_A$-1), ($Z_A$-2), ($Z_A$-3), and ($Ar_A$-1), $X_A$'s each independently represent a nitrogen atom, a bromine atom, or a phosphor atom;
$Y_A$ and Yd each independently represent a single bond, a substituted or unsubstituted alkylene group having 1 to 30 carbon atoms, a substituted or unsubstituted arylene group having 6 to 30 carbon atoms, or a substituted or unsubstituted heterocyclic group having 4 to 30 carbon atoms;
$R_{A1}$, $R_{A2}$, and $R_{A3}$ each independently represent a hydrogen atom, a substituted or unsubstituted alkyl group having 1 to 30 carbon atoms, a substituted or unsubstituted aryl group having 6 to 30 carbon atoms, or a substituted or unsubstituted heterocyclic group having 4 to 30 carbon atoms, and the adjacent groups out of $R_{A1}$, $R_{A2}$, and $R_{A3}$ may be bonded to each other to form a saturated or unsaturated carbocycle;

$R_A'$ and $R_A''$ each independently represent a hydrogen atom, a hydroxyl group, a substituted or unsubstituted alkyl group having 1 to 30 carbon atoms, or a substituted or unsubstituted aryl group having 6 to 30 carbon atoms;

(B1-1)

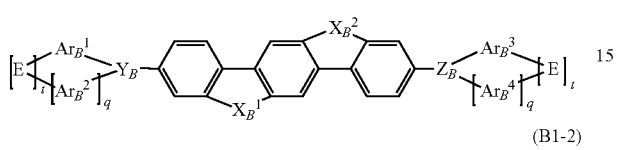

(B1-2)

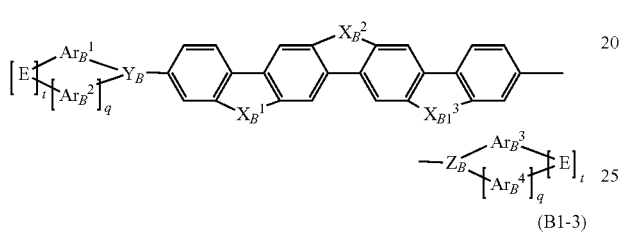

(B1-3)

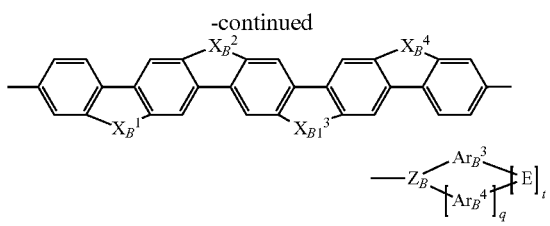

$X_B^1$, $X_B^2$, $X_B^3$, and $X_B^4$ each independently represent $B(R_B^1)$, $C(R_B^1)_2$, $S(R_B^1)_2$, $C=O$, $C=NR_B^1$, $C=C(R_B^1)_2$, O, S, S=O, $SO_2$, $N(R_B^1)$, $P(R_B^1)$, $P(=O)R_B^1$, $P(=S)R_B^1$, or a group formed by a combination of 2 to 4 groups out of these groups;

$Y_B$ and $Z_B$ each independently represent N, P, P=O, $PF_2$, P=S, As, As=O, As=S, Sb, Sb=O, Sb=S, C=O, O, S, Se, Te, S=O, $SO_2$, $SeO_2$, Te=O, or $TeO_2$;

$Ar_B^1$, $Ar_B^2$, $Ar_B^3$, and $Ar_B^4$ each independently represent an aromatic hydrocarbon ring group or an aromatic heterocyclic group;

E's each independently represent a single bond, $N(R_B^1)$, O, S, $C(R_B^1)_2$, $Si(R_B^1)_2$, or $B(R_B^1)$;

$R_B^1$'s each independently represent a hydrogen atom or a substituent;

q and r each independently represent 0 or 1;

t's each independently represent 0 or 1.

2. The organic electroluminescent element according to claim 1, wherein the compound represented by the general formula (B1-1), (B1-2), or (B1-3) is represented by the following general formula (B2-1), (B2-2), or (B2-3);

(B2-1)

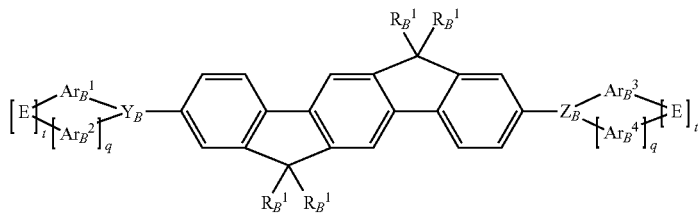

(B2-2)

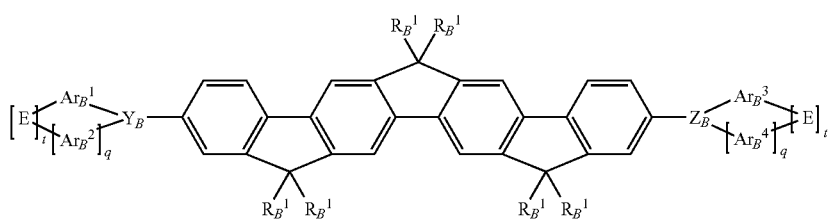

(B2-3)

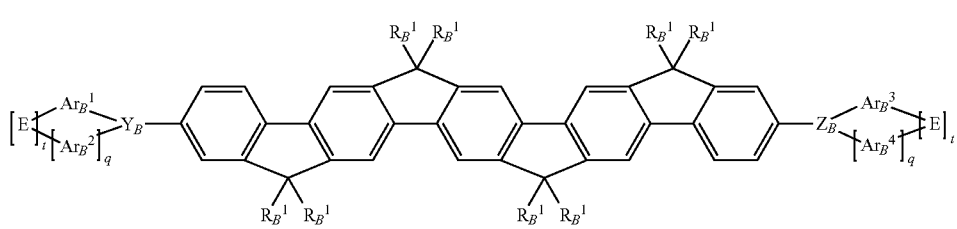

where in the general formulae (B2-1), (B2-2), and (B2-3), $Y_B$, $Z_B$, $Ar_B^1$, $Ar_B^2$, $Ar_B^3$, $Ar_B^4$, E, $R_B^1$, q, r, and t have the same meanings as $Y_B$, $Z_B$, $Ar_B^1$, $Ar_B^2$, $Ar_B^3$, $Ar_B^4$, E, $R_B^1$, q, r, and t in the general formulae (B1-1), (B1-2), and (B1-3).

3. The organic electroluminescent element according to claim 1, wherein the compound represented by the general formula (A) is represented by the following general formula (A1);

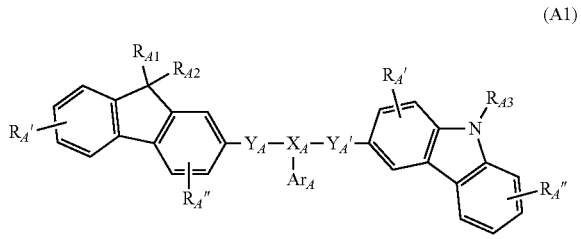

(A1)

where in the general formula (A1), $Ar_A$, $X_A$, $Y_A$, $R_{A1}$, $R_{A2}$, $R_{A3}$, $R_A'$, and $R_A''$ have the same meanings as $Ar_A$, $X_A$, $Y_A$, $R_{A1}$, $R_{A2}$, $R_{A3}$, $R_A'$, and $R_A''$ in the general formula (A); $Y_A'$ has the same meaning as $Y_A$.

4. The organic electroluminescent element according to claim 1, wherein $X_A$ in the general formula (A) or (A1) represents a nitrogen atom.

5. The organic electroluminescent element according to claim 1, wherein $Ar_A$ in the general formula (A) or (A1) represents a substituted or unsubstituted aryl group.

6. The organic electroluminescent element according to claim 1, wherein $Y_A$, Yd, and $Y_A'$ in the general formula (A) or (A1) each independently represent a single bond or an unsubstituted arylene group having 6 to 12 carbon atoms.

7. The organic electroluminescent element according to claim 1, wherein $R_{A1}$, and $R_{A2}$ in the general formula ($Z_A$-1), ($Z_A$-2), ($Z_A$-3), or (A1) each independently represent a substituted or unsubstituted alkyl group having 1 to 30 carbon atoms, or a substituted or unsubstituted aryl group having 6 to 30 carbon atoms.

8. The organic electroluminescent element according to claim 1, wherein $R_{A3}$'s in the general formula ($Z_A$-1), ($Z_A$-2), ($Z_A$-3), or (A1) each independently represent a substituted or unsubstituted aryl group having 6 to 30 carbon atoms.

9. The organic electroluminescent element according to claim 1, wherein $Y_B$ and $Z_B$ in the general formula (B1-1), (B1-2), (B1-3), (B2-1), (B2-2), or (B2-3) represent N.

10. The organic electroluminescent element according to claim 1, wherein $Ar_B^1$, $Ar_B^2$, $Ar_B^3$, and $Ar_B^4$ in the general formula (B1-1), (B1-2), (B1-3), (B2-1), (B2-2), or (B2-3) each independently represent an aromatic hydrocarbon ring group.

11. A light emitting device using the organic electroluminescent element according to claim 1.

12. A display device using the organic electroluminescent element according to claim 1.

13. An illumination device using the organic electroluminescent element according to claim 1.

* * * * *